United States Patent [19]

Matassa

[11] Patent Number: 5,047,402
[45] Date of Patent: Sep. 10, 1991

[54] CYCLIC AMIDES AS MEDICAMENTS

[75] Inventor: Victor G. Matassa, Chadds Ford, Pa.

[73] Assignee: ICI Americas Inc., Wilmington, Del.

[21] Appl. No.: 337,193

[22] Filed: Apr. 12, 1989

Related U.S. Application Data

[63] Continuation-in-part of Ser. No. 180,875, Apr. 13, 1988, abandoned.

[51] Int. Cl.$^5$ ............... A61K 31/55; C07D 225/00; C07D 401/00; C07D 209/18
[52] U.S. Cl. ................. 514/212; 540/451; 546/201; 548/495; 514/323; 514/414
[58] Field of Search .......... 540/451; 546/201; 548/495; 514/212, 323, 414

[56] References Cited

U.S. PATENT DOCUMENTS 3,347,866  10/1967  Hester .................... 540/524 X
4,803,198  2/1989   Ohlendorf et al. ........ 546/201 X

FOREIGN PATENT DOCUMENTS

179619A1  4/1986  European Pat. Off. .

OTHER PUBLICATIONS

J. L. Marx, *Science* (1982) 215, 1380: "The Leukotrienes in Allergy and Inflammation."
J. A. Cook et al., *J. Pharm. Exp. Ther.* (1985) 235, 470: "Protective Effect of a Selective Leukotriene Antagonist in Endotoxemia in the Rat."
C. Denzlinger et al., *Science* (1985) 230, 330: "Leukotrienes as Mediators in Tissue Trauma."
R. D. Krell, *J. Pharm. Exp. Ther.* (1979) 211, 436: "Pharmacologic Characterization of Isolated Rhesus Monkey Brochial Smooth Muscle."
D. Aharony et al., *Fed. Proc.* (1987) 46, 691: "Inhibition of $^3$H-Leukotriene (LT) D$_4$ Binding to Guinea-Pig Lung Membrane Receptors by the Novel Leukotriene Antagonist ICI 198,615".
Yung-chi Cheng and W. H. Prusoff, *Biochem. Pharmacol.* (1973) 22, 3099-3108: "Relationship Between the Inhibition Constant (K$_I$) and the Concentration of Inhibitor Which Causes 50 Per Cent Inhibition (I$_{50}$) of the Enzymatic Causes 50 Reaction."

*Primary Examiner*—Mary C. Lee
*Assistant Examiner*—Robert C. Whittenbaugh
*Attorney, Agent, or Firm*—Rosemay M. Miano; Thomas E. Jackson

[57] ABSTRACT

This invention provides a series of novel cyclic amides of formula I in which the group >Z—Y—X< is selected from >C=CH—N<, >N–CH=CH<, >C=N—N< and >N—N=C< and the other radicals have the meanings defined in the following specification. The compounds of formula I are leukotriene antagonists. The invention also provides pharmaceutically acceptable salts of the formula I compounds; pharmaceutical compositions containing the formula I compound, or their salts, for use in the treatment of, for example, allergic or inflammatory diseases, or endotoxic or traumatic shock conditions; and processs for the manufacture of the formula I compounds, as well as intermediates for use in such manufacture.

14 Claims, No Drawings

CYCLIC AMIDES AS MEDICAMENTS

This application is a continuation-in-part of U.S. Ser. No. 07/180,875, filed Apr. 13, 1988, and now abandoned.

BACKGROUND AND SUMMARY OF THE INVENTION

This invention concerns novel cyclic amide derivatives, and, particularly, certain lactams and thiolactams, which antagonize the actions of one or more of the arachidonic acid metabolites known as leukotrienes (hereinafter referred to as "leukotriene antagonist properties"). The novel derivatives are useful whenever such antagonism is desired. Thus, such compounds may be of value in the treatment of those diseases in which leukotrienes are implicated, for example in the treatment of allergic disorders, such as, for example, asthma, or of inflammatory diseases, or of endotoxic or traumatic shock conditions. The invention also provides pharmaceutical compositions treatments, and processes and intermediates for the manufacture of the novel derivatives.

In European Patent Application publication number 0 179 619 Al are disclosed N-acylated derivatives of a series of indoles, indazoles and indolines having an amino group in the benzenoid ring and which possess leukotriene antagonizing properties. I have now discovered a series of indoles and indazoles which have an aliphatic cyclic amide substituent in the benzenoid ring and which unexpectedly possess the property of antagonizing one or more of the arachidonic acid metabolites known as leukotrienes and this is the basis for my invention.

DESCRIPTION OF THE INVENTION

According to the invention there is provided a compound of formula I (formula set out, together with other formulae referred to by Roman numerals, on pages following the Examples) wherein:

the group $>Z-Y-X<$ is selected from a group consisting of:
(a) $>C=CR^a-N<$,
(b) $>N-CR^a=C<$,
(c) $>C=N-N<$ and
(d) $>N-N=C<$;

in which ">" indicates two separate bonds;

the radicals $R^a$, if present, and $R^b$ are together selected from a group consisting of
(i) $R^a$, if present, and $R^b$ are each hydrogen,
(ii) $R^a$ is chloro and $R^b$ is hydrogen,
(iii) $R^a$ is bromo and $R^b$ is hydrogen and
(iv) $R^a$, if present, and $R^b$ are each chloro;

Q is oxygen or sulfur;

the groups $R^1$ and $R^9$ are each independently selected from a group consisting of hydrogen, (1-6C)alkyl optionally containing a double or triple bond, (3-6C)cycloalkyl and (3-6C)cycloalkyl(1-4C)alkyl wherein a cycloalkyl group or the cycloalkyl portion of a cycloalkylalkyl group may optionally contain a double bond and may optionally bear 1 or 2 (1-3C)alkyl groups;

$R^3$ is hydrogen or (1-C)alkyl;

the values of m and n are independently selected from a group of integers consisting of 1, 2 and 3;

$R^{11}$ is selected from hydrogen, (1-4C)alkoxy, (1-2C)alkyl and hydroxy:

$R^{12}$ is selected from a group consisting of (6-12C)aryl, heteroaryl, and (6-12C)aryl(1-4C)alkyl, in any of which the aromatic or heteroaromatic moiety may optionally bear 1 or 2 substituents selected from a group consisting of halogeno, (1-4C)alkyl, (1-4C)alkoxy, trifluoromethyl and amino;

and salts thereof, especially pharmaceutically acceptable salts.

It will be appreciated that certain of the compounds of formula I may contain an asymmetrically substituted carbon atom, may exist in, and be isolated in, optically-active and racemic forms. In addition, it will be appreciated that certain compounds of formula I, for example, those containing a double bond, may exist in, and be isolated in, separate stereoisomeric forms ('E' and 'Z') about that group. Some compounds may exist in more than one tautomeric form. Some compounds may exhibit polymorphism. It is to be understood that the present invention encompasses any racemic, optically-active, tautomeric, polymorphic or stereoisomeric form, or mixtures thereof, which form possesses leukotriene antagonist properties, it being well known in the art how to prepare optically-active forms (for example, by resolution of the racemic form or by synthesis from optically-active starting materials) and individual 'E' and 'Z' stereoisomers (for example, by chromatographic separation of a mixture thereof) and how to determine the leukotriene antagonist properties by the standard tests described hereinafter.

In this specification $R^1$, $R^2$, et cetera stand for generic radicals and have no other significance. It is to be understood that the generic term "(1-6C)alkyl includes both straight and branched chain alkyl radicals but references to individual alkyl radicals such as "propyl" embrace only the straight chain ("normal") radical, branched chain isomers such as "isopropyl" being referred to specifically. A similar convention applies to other generic groups, for example, "alkylene" and "alkenylene" et cetera. Heteroaryl means a monocyclic or fused bicyclic ring system of from 5 to 11 atoms containing at least one 5- or 6-membered aromatic ring and consisting of from 1 to 10 carbons and from 1 to 4 heteroatoms each of which is selected independently from a group consisting of oxygen, sulfur, and nitrogen. Halogeno is fluoro, chloro, bromo or iodo.

Particular values for $R^1$ or $R^9$ when it is (1-6C)alkyl include, for example, methyl, ethyl, propyl, isopropyl, butyl, 1-methylpropyl, 2-methylpropyl, pentyl, 1-ethylpropyl, 3-methylbutyl, hexyl, and 4-methylpentyl; and when the alkyl group contains an optional double or triple bond, particular values include allyl, 2-methylprop-2-enyl, 3-methylbut-3-enyl and 2-propynyl.

Particular values for $R^1$ or $R^9$ when it is (3-6C)cycloalkyl include, for example, cyclopropyl, cyclobutyl, cyclopentyl, and cyclohexyl; and when the cycloalkyl group contains an optional double bond or alkyl substituent, particular values include cyclopentenyl, cyclohexenyl and methylcyclobutyl.

Particular values for $R^1$ or $R^9$ when it is (3-6C)cycloalkyl(1-4C)alkyl include, for example, cyclopropylmethyl, cyclobutylmethyl, cyclopentylmethyl, cyclohexylmethyl, 1-cyclopentylethyl and 2-cyclopentylethyl; and when the cycloalkyl portion contains an optional double bond or alkyl substituent, particular values include methylcyclopentylethyl.

Particular values for $R^3$ when it is (1-3C)alkyl include methyl, ethyl and propyl.

Particular values for $R^{11}$ when it is (1–4C)alkoxy include, for example, methoxy, ethoxy and propoxy: and when it is (1–2C)alkyl, particular values include methyl and ethyl.

Particular values for $R^{12}$ when it is (6–12C)aryl include, for example, phenyl and naphthyl: when $R^{12}$ is heteroaryl, thienyl, furyl and pyridyl: and when $R^{12}$ is (6–12C)aryl(1–4C)alkyl, phenylmethyl, 2-phenylethyl and 3-phenylpropyl. Particular values for an optional substituent on the aromatic or heteroaromatic portion of $R^{12}$ include, for example, fluoro, chloro, bromo, methyl, ethyl, methoxy, ethoxy, trifluoromethyl and amino.

More particular values for the radicals for a compound of formula I are independently selected from those listed below.

More particular values and ranges for the values of $R^1$ and $R^9$ are each independently selected from a group consisting of hydrogen, (1–4C)alkyl optionally containing a double bond, (3–5C)cycloalkyl and (3–5C)cycloalkyl(1–2C)alkyl.

More particular values for $R^3$ include hydrogen and methyl.

More particular values and ranges for the values of $R^{11}$ include hydrogen and (1–2C)alkoxy.

More particular values for $R^{12}$ include phenyl (optionally substituted by methyl, chloro, bromo, fluoro or methoxy), pyridyl, and thienyl.

Typical values for the radicals and groups for a compound of formula I are independently selected from those listed below.

A typical value for $R^a$ is hydrogen or chloro, and for $R^b$ is hydrogen.

A typical value for $R^1$ is methyl, ethyl or propyl: for $R^3$ is hydrogen: and for $R^9$ is methyl or propyl.

A typical value for m is the integer 1, and for n is the integer 1 or 2.

A typical value for $R^{11}$ is methoxy.

A typical value for $R^{12}$ is 2-methylphenyl, 2-chlorophenyl or 2-bromophenyl.

It is preferred that when $R^{12}$ is a substituted phenyl that the substituent be in the "2" position.

It will be appreciated that within the above definitions there are included a number of sub-groups of compounds, for example (a) indoles of formula Ia, (b) inverted indoles of formula Ib, (c) indazoles of formula Ic, and (d) inverted indazoles of formula Id, wherein Q, $R^a$, $R^b$, $R^1$, $R^3$, n, m, $R^9$, $R^{11}$, and $R^{12}$ have any of the values defined above for a compound of formula I, together with the pharmaceutically acceptable salts thereof.

A particular subgroup of compounds of formula I (or of formula Ia, Ib, Ic or Id) is one in which Q is oxygen, $R^a$ is hydrogen and $R^b$ is hydrogen.

A preferred subgroup is that of compounds of formula Ib. Preferred values for radicals and groups of a compounds of formula Ib include, for example, those listed above as typical values for a compound of formula I.

Preferred compounds of the invention include 3-methoxy-N-(2-methylphenylsulfonyl)-4-[1-propyl-5-(1-propyl-2-oxopyrrolidin-3-ylmethyl)indol-3-ylmethyl]benzamide; 3-methoxy-4-[5-(1-methyl-2-oxopiperidin-3-ylmethyl)-1-propylindol-3-ylmethyl]-N-(2-methylphenylsulfonyl)benzamide; and 4-[5-(1-ethyl-2-oxopyrrolidin-3-ylmethyl)-1-propylindol-1-propylindol-3-ylmethyl]-3-methoxy-N-(2-methylphenylsulfonyl)benzamide; and the pharmaceutically acceptable salts thereof.

Examples of suitable pharmaceutically acceptable salts are salts formed with bases which form a physiologically acceptable cation, such as alkali metal (especially sodium or potassium), alkaline earth metal (especially calcium or magnesium), aluminum or ammonium salts, as well as salts made with appropriate organic bases such as triethylamine, morpholine, piperidine or triethanolamine. For those compounds of formula I which are sufficiently basic, examples of suitable pharmaceutically acceptable salts include acid-addition salts such as those made with a strong acid, for example hydrochloric, sulfuric or phosphoric acid.

The compounds of formula I may be made by processes which include processes known in the chemical art for the production of structurally analogous heterocyclic compounds. Such processes for the manufacture of a compound of formula I as defined above are provided as further features of the invention and are illustrated by the following procedures in which the meanings of generic radicals are as defined above:

(A) Reacting a compound of formula III wherein $R^{10}$ is carboxy (which compound is hereinafter referred to as "acid of formula III") with a sulfonamide derivative of formula $R^{12}·SO_2.NH_2$ in the presence of a dehydrating agent or reacting a reactive derivative of an acid of formula III with a sulfonamide, or a salt thereof, of formula $R^{12}·SO_2.NH_2$.

Thus, for example, a free acid of formula III may be reacted with a suitable dehydrating agent, for example, with dicyclohexylcarbodiimide or 1-(3-dimethylaminopropyl)-3-ethylcarbodiimide, or with a hydrochloride or hydrobromide salt thereof, optionally together with an organic base, for example, 4-dimethylaminopyridine, and with a sulfonamide of formula $R^{12}·SO_2.NH_2$ in the presence of a suitable solvent or diluent, for example, methylene chloride at a temperature in the range of, for example, 10 to 50° C., but preferably at or near ambient temperature.

Alternatively, a reactive derivative of an acid of formula III, for example, an acid halide (such as the acid chloride), acid anhydride or a mixed acid anhydride (such as that formed from N,N-diphenylcarbamic acid and the acid of formula I by reaction of the sodium salt of the latter acid with N,N-diphenylcarbamoylpyridinium chloride), may be reacted with an alkali metal salt (such as the lithium, sodium or potassium salt) of the appropriate sulfonamide of formula $R^{12}·SO_2.NH_2$, conveniently at or near ambient temperature and in a suitable solvent or diluent, for example, tetrahydrofuran, dimethylformamide or methylene chloride.

An acid of formula III wherein $R^{10}$ is a carboxy group may be obtained by decomposing a suitable ester of formula III in which $R^{10}$ is $COOR^h$ wherein $R^h$ is a conveniently removed acid protecting group (which compound is hereinafter referred to as "ester of formula III"), for example, phenyl, benzyl, or (1–6C)alkyl optionally bearing an acetoxy, (1–4C)alkoxy or (1–4C)alkylthio substituent. A particular value for $R^h$ is, for example, methyl, ethyl, propyl, t-butyl, acetoxymethyl, methoxymethyl, 2-methoxyethyl, methylthiomethyl, phenyl, or benzyl.

The starting acids of formula III wherein $R^{10}$ is carboxy are active as leukotriene antagonists, and they are included within the scope of the invention. In addition, certain of the corresponding esters of formula III wherein $R^{10}$ is $COOR^h$ may be active in their own right as leukotriene antagonists (such as, for example, by in vivo conversion to the corresponding carboxylic acid), for example, those wherein $R^h$ is (1–6C)alkyl, and they are also included within the scope of the invention.

It will be appreciated that the decomposition of an ester of formula III can be performed using any one of a variety of procedures well known in the art of organic chemistry. Thus, it may be carried out, for example, by conventional hydrolysis under acid or base conditions, adjusted as necessary to minimize any hydrolytic removal of other functional groups in the molecule. Also, when $R^h$ is methyl, the ester may be decomposed by nucleophilic demethylation with, for example, lithium thioethoxide in a solvent such as N,N'-dimethylpropyleneurea. Alternatively, it may in certain circumstances, for example, when $R^h$ is t-butyl, be possible to carry out the decomposition by thermal means, for example, by heating the ester of formula III at a temperature of, for example, 100–150° C., alone or in a suitable solvent or diluent such as diphenylether. In addition, when $R^h$ is t-butyl, the decomposition may be performed, for example, by using trimethylsilyl triflate and then water, in a conventional manner. Still further, in certain circumstances, for example, when $R^h$ is benzyl, it may be possible to carry out the decomposition by reductive means, for example, by the use of hydrogen at about atmospheric pressure in the presence of a suitable catalyst, such as palladium or platinum, conveniently on charcoal as a support.

A preferred method for decomposing an ester of formula III comprises reacting the ester with a suitable base, for example, an alkali or alkaline earth metal hydroxide or carbonate (such as lithium hydroxide, potassium hydroxide, sodium hydroxide, calcium hydroxide or potassium carbonate) in a suitable aqueous solvent or diluent, for example, water, optionally together with a water-miscible alkanol, glycol, ketone or ether (such as methanol, ethanol, ethylene glycol, 2-methoxyethanol, acetone, methyl ethyl ketone, tetrahydrofuran or 1,2-dimethoxyethane), at a temperature of, for example, 15–100° C. and conveniently at or near ambient temperature. When such a method is employed, the resulting carboxylic acid of formula III, wherein $R^{10}$ is a carboxy group, is initially obtained as the corresponding salt of the base used for the hydrolysis and may be isolated as such or converted to the free acid form by a conventional acidification procedure, for example, by reaction with a suitable strong acid such as hydrochloric or sulfuric acid.

(B) Reduction of the double bond of a compound of formula I in which $R^1$ or $R^9$ contains one double bond to provide a corresponding compound of formula I in which $R^1$ or $R^9$ contains no double bond, or reduction of a double bond of a compound corresponding to a compound of formula I, but in which the link between the cyclic amide and the benzenoid ring contains a double bond, to afford a corresponding compound of formula I.

Preferred reduction conditions include, for example, catalytic hydrogenation over palladium on carbon in a suitable solvent such as methanol, ethanol, ethyl acetate, or tetrahydrofuran at ambient temperature, and, optionally, the addition of an equivalent of a base, such as, for example, potassium hydroxide or triethylamine.

(C) For a compound of formula I wherein $>Z-Y-X-<$ has the value (b) or (d) and $R^9$ is not hydrogen, reacting a corresponding imine of formula I wherein $>Z-Y-X-<$ has the value (b) or (d) and $R^9$ is hydrogen with a reagent of formula $R^9 \cdot U$, wherein U is a suitable leaving group, for example, chloro, bromo, iodo, methanesulfonyloxy or p-toluenesulfonyloxy.

The reaction is preferably performed in the presence of a suitable base, for example, an alkali metal hydride such as sodium or potassium hydride in a suitable inert solvent or diluent, for example, tetrahydrofuran 1,2-dimethoxyethane, N-methylpyrrolidone, or N,N-dimethylformamide. Alternatively, the compound of formula I may be used in the form of its preformed anhydrous alkali dimetal salt, for example, by prior reaction with a suitable base such as sodium or potassium methoxide, t-butoxide or hydride, or butyl lithium, in which case a wider range of conventional solvents or diluents may be employed for the reaction with the alkylating agent. In either case, the alkylation is generally performed at a temperature in the range of, for example, −10 to 40° C. and, conveniently, at or near ambient temperature.

It may be desired to optionally use a protecting group during all or portions of the above described processes (A)-(C): the protecting group then may be removed when the final compound is to be formed.

Pharmaceutically acceptable salts may be obtained using standard procedures well known in the art, for example, by reacting a compound of formula I with a suitable base affording a physiologically acceptable cation or by reacting a sufficiently basic compound of formula I with a suitable acid affording a physiologically acceptable anion.

If not commercially available, the necessary starting materials for the above procedures may be made by procedures which are selected from standard techniques of heterocyclic chemistry, techniques which are analogous to the synthesis of known, structurally similar compounds, or techniques which are analogous to the above described procedures or the procedures described in the examples.

In general, the preparation of a starting material of formula III may begin with an appropriate heterocycle having a simple substituent at the position of attachment of the side chain containing the cyclic amide group, for example, 5-cyanoindole. By introduction of the required substituents at X and Z on the heterocyclic ring, followed by elaboration of the side chain joined to the benzenoid ring, the desired starting material may be obtained. It will be clear to one skilled in the art that the order of steps for the introduction onto the heterocyclic ring of the various groups at X and Z and the elaboration of the side chain containing the cyclic amide may be varied according to considerations of convenience, protecting groups, presence of reactive groups, etc. The introduction of each group will therefore be described independently.

Routes for the introduction of substituents at positions X and Z of the heterocyclic rings (in which $R^a$, if present, and $R^b$ are each hydrogen) are illustrated in Schemes Ia–Id. In these schemes, $R^c$ may represent the side chain containing the cyclic amide group or, more preferably, an intermediate or precursor to that group, such as, for example, cyano, formyl, or carbomethoxy, as described hereinbelow; U may represent a leaving group, especially bromo: and V may represent a halogeno group.

Intermediates which are indoles may be prepared by using sequences illustrated in Scheme Ia. Thus, an indole of formula 20 may be formylated to provide a 3-formylindole of formula 21, which may be further converted into a benzylated derivative of formula 22 by alkylation with a substituted benzyl compound of formula 23. By further elaboration of the 3-formyl group into a group of formula $R^9$ using conventional methods, a compound of formula 22 may be converted into a corresponding compound of formula Va. Alternatively, an indole of formula 20 may be alkylated at the 3-position using, for example, silver carbonate, and a sufficiently reactive alkylating agent of formula $R^9 \cdot V$, especially wherein V is bromo or chloro, to afford an indole of formula 25. An indole of formula 25 may be alkylated with a compound of formula 23 to provide an intermediate of formula Va.

Intermediates which are "inverted indoles" may be prepared by using a sequence illustrated in Scheme Ib. Thus, an indole of formula 26 may be alkylated using, for example, silver carbonate, and a compound of formula 23 to afford an indole of formula 27. By introduction of the $R^9$ group using a conventional procedure, including a similar procedure to process (C), an indole of formula 27 may be converted into a corresponding indole of formula Vb.

Intermediates which are indazoles may be prepared using a sequence illustrated in Scheme Ic. Thus, an indazole of formula 29 may be halogenated to afford an indazole of formula 30, especially one wherein V is chloro or bromo. An indazole of formula 30, conveniently as the sodium salt, may be treated with an alkylating agent of formula 23 to afford an indazole of formula 31. To obtain an indazole of formula Vc wherein $R^9$ is hydrogen, the V-group of an indazole of formula 31 may be removed reductively. Otherwise, an indazole of formula 31 may be substituted at the 3-position by a transition metal catalyzed cross coupling reaction, followed by elaboration of the group introduced as necessary to provide $R^9$ using conventional methodology.

Intermediates which are "inverted indazoles" may be prepared by using a sequence illustrated in Scheme Id. Thus, an indazole of formula 33 may be halogenated to afford an indazole formula 34, especially one wherein V is bromo. An indazole of formula 34, conveniently as the sodium salt, may be alkylated with a reagent of formula $U.R^9$ to afford a corresponding indazole of formula 35. By using a cross coupling reaction using a transition metal catalyst such as, for example, dichloro[1,1'-bis(diphenylphosphino)ferrocene]palladium(II), and a compound of formula 23 wherein U is, for example, bromo, an indazole of formula 34 may be converted into an indazole of formula Vd.

An intermediate of formula V wherein $R^a$, if present, and $R^b$ are each hydrogen (i.e., a selected intermediate of formula Va, Vb, Vc or Vd) may be converted into a corresponding starting material of formula III by a conventional method, such as, for example, described in the examples and described below. A compound of formula V in which $R^c$ is cyano may be reduced to a corresponding compound of formula V in which $R^c$ is formyl using, for example, a similar method to the one described in Example 1.b., to serve as a general intermediate for the introduction of the side chain containing the cyclic amide group. Examples of routes to corresponding compounds of formula III, wherein Q is oxygen and $R^{10}$ is $COOR^h$ are outlined in Scheme II. Intermediates of formula III, wherein $R^a$, if present, and $R^b$ are hydrogen and Q is oxygen and $R^{10}$ is $COOR^h$ conveniently may be converted into corresponding intermediates of formula III wherein Q is oxygen and $R^{10}$ is $COOR^h$ and wherein $R^a$ is chloro and $R^b$ is hydrogen; wherein $R^a$ is bromo and $R^b$ is hydrogen and wherein $R^a$, if present, and $R^b$ are each chloro. Thus, an ester of formula III wherein Q is oxygen and $R^{10}$ is $COOR^h$ and wherein $R^a$ is present and $R^a$ and $R^b$ are each hydrogen may be treated with one molar equivalent of N-chlorosuccinimide or N-bromosuccinimide, respectively, in an inert solvent, for example in a manner similar to that described in Example 6.a., to afford a corresponding ester of formula III wherein Q is oxygen and $R^{10}$ is $COOR^h$ wherein $R^a$ is chloro and $R^b$ is hydrogen or wherein $R^a$ is bromo and $R^b$ is hydrogen, respectively. Similarly, an ester of formula III wherein $>Z-Y-X<$ is $>N-CR^a=C<$, Q is oxygen and $R^{10}$ is $COOR^h$ and wherein $R^a$ and $R^b$ are both hydrogen may be treated with at least two molar equivalents of N-chlorosuccinimide in an inert solvent to provide a corresponding ester of formula III wherein Q is oxygen and $R^{10}$ is $COOR^h$ and wherein $R^a$ and $R^b$ are both chloro. A lactam ester of formula III wherein Q is oxygen and $R^{10}$ is $COOR^h$ may be converted into a corresponding thiolactam ester of formula III wherein Q is sulfur and $R^{10}$ is $COOR^h$ by treatment with Lawesson's reagent, for example, as described in Example 12.a.

As stated previously, the compounds of formula I possess leukotriene antagonist properties. Thus, they antagonize at least one of the actions of one or more of the arachidonic acid metabolites known as leukotrienes, for example, $C_4$, $D_4$, and/or $E_4$, which are known to be powerful spasmogens (particularly in the lung), to increase vascular permeability and which have been implicated in the pathogenesis of asthma and inflammation (see J. L. Marx, *Science*, 1982, 215, 1380–1383) as well as of endotoxic shock (see J. A. Cook, et al., *J. Pharma col. Exp. Ther.*, 1985, 235, 470) and traumatic shock (see C. Denzlinger, et al., *Science* 1985, 230, 330). Thus, the compounds of formula I may be useful in the treatment of diseases in which leukotrienes are implicated and in which antagonism of their action is desired. Such diseases include, for example, allergic pulmonary disorders such as asthma, hay fever and allergic rhinitis and certain inflammatory diseases such as bronchitis, ectopic and atopic eczema, psoriasis, as well as vasospastic cardiovascular disease, and endotoxic and traumatic shock conditions.

The compounds of formula I are potent leukotriene antagonists and are useful whenever such activity is desired. For example, the compounds of formula I are of value as pharmacological standards for the development and standardization of new disease models and assays for use in developing new therapeutic agents for treating the diseases in which the leukotrienes are implicated.

When used in the treatment of one or more of the above mentioned diseases, a compound of formula I is generally administered as an appropriate pharmaceutical composition which comprises a compound of formula I as defined hereinbefore together with a pharmaceutically acceptable diluent or carrier, the composition being adapted for the particular route of administration chosen. Such compositions are provided as a further feature of the invention. They may be obtained employing conventional procedures and excipients and binders and may be in a variety of dosage forms. For example, they may be in the form of tablets, capsules, solutions or suspensions for oral administration; in the form of suppositories for rectal administration: in the form of sterile solutions or suspensions for administration by intravenous or intramuscular injection or infusion; in the form of aerosols or nebuliser solutions or suspensions for administration by inhalation; and in the form of powders together with pharmaceutically acceptable inert solid diluents such as lactose for administration by insufflation.

For oral administration a tablet or capsule containing up to 250 mg (and typically 5 to 100 mg) of a compound of formula I may conveniently be used. Similarly, for intravenous or intramuscular injection or infusion a sterile solution or suspension containing up to 10% w/w (and typically 0.05 to 5% w/w) of a compound of formula I may conveniently be used.

The dose of compound of formula I to be administered will necessarily be varied according to principles well known in the art taking account of the route of administration and the severity of the condition and the size and age of the patient under treatment. However, in general, a compound of formula I will be administered to a warm-blooded animal (such as man) so that a dose in the range of, for example, 0.05 to 25 mg/kg (and usually 0.5 to 10 mg/kg) is received.

The leukotriene antagonist properties of a compound of formula I may be demonstrated using standard tests. Thus, for example, they may be demonstrated in vitro using the standard guinea-pig tracheal strip preparation described by Krell (*J. Pharmacol. Exp. Ther.*, 1979, 211, 436) and as also described in European Patent Application publication number 0 179 619 A1.

The selectivity of action of these compounds as leukotriene antagonists as opposed to non-specific smooth muscle depressants may be shown by carrying out the above in vitro procedure using the non-specific spasmogen barium chloride at a concentration of $1.5 \times 10^{-3}$M, again in the presence of indomethacin at $8 \times 10^{-6}$M.

Alternatively, the antagonistic properties of a compound of formula I can be demonstrated in vitro by a receptor-ligand binding assay described by Aharony (*Fed. Proc.* 46: 691, (1987)). According to this procedure, membrane fractions, containing the $LTD_4/E_4$ receptors, are prepared from guinea-pig lung parenchyma and incubated for 30 minutes at 22° C. with 1nM $^3H$-$LTD_4$ in the absence or presence of tested antagonist. Specific binding, determined under conditions that prevent enzymatic metabolism of $^3H$-$LTD_4$, is the net result of total $^3H$-$LTD_4$ binding minus nonspecific binding determined in the presence of 1-2000 fold excess unlabelled $LTD_4$. Each assay is done in duplicate and results (Ki values) are typically a mean of several such determinations in individual receptor batches.

The % inhibition by a tested antagonist, relative to control binding (vehicle alone), is expressed as a fraction of log[antagonist] concentration (in molar units) and the half-maximal inhibition ($IC_{50}$) determined by computerized non-linear least-square analysis. The binding constant (Ki) is then calculated from $IC_{50}$ by the Cheng-Prusoff equation:

$$Ki = \frac{IC_{50}}{\left[1 + \frac{[L]}{Kd}\right]}$$

where [L] is $^3H$-$LTD_4$ concentraton and Kd is the affinity constant of $LTD_4$ to this receptor, determined separately for each batch. (*Biochem. Pharmacol.* 22: 3099-3108, 1973).

In general, the compounds of formula I tested demonstrated statistically significant activity as $LTC_4$, $LTD_4$ and/or $LTE_4$ antagonists in one the above tests at a concentration of about $10^{-7}$M or much less. For example, in the above described test, a Ki value of $10^{-9}$M was determined for the compound of Example 1.

Activity as a leukotriene antagonist may also be demonstrated in vivo in laboratory animals, for example, in a routine guinea-pig aerosol test in which guinea-pigs are pre-dosed with test compound (generally between 15 minutes to 1 hour) before an aerosol challenge of leukotriene $LTD_4$ (starting with 2 ml of a 30 microgram/ml solution) and the effect of the test compound on the average time of leukotriene initiated change in breathing pattern (such as onset of dyspnoea) recorded and compared with that in undosed, control guinea-pigs. In general, compounds of formula I tested produced a significant increase in the time of onset of leukotriene initiated breathing changes following either oral or intravenous administration or by inhalation at a dose of about 100 mg/kg, or much less, without any indication of untoward side-effects at several multiples of the minimum effective dose.

The invention will now be illustrated by the following non-limiting examples in which, unless stated otherwise:

(i) temperatures are given in degrees Celsius (° C.); operations were carried out at room or ambient temperature, that is, at a temperature in the range of 18–25° C.;

(ii) evaporation of solvent was carried out using a rotary evaporator under reduced pressure (600–4000 pascals: 4.5–30 mm Hg) with a bath temperature of up to 60° C.;

(iii) flash chromatography was carried out on Merck Kieselgel (Art 9385) and column chromatography on Merck Kieselgel 60 (Art 7734); [these materials were obtained from E. Merck, Darmstadt, W. Germany]; thin layer chromatography (TLC) was carried out on Analtech 0.25 mm silica gel GHLF plates (Art 21521), obtainable from Analtech, Newark, DE, USA;

(iv) in general, the course of reactions was followed by TLC and reaction times are given for illustration only;

(v) melting points are uncorrected and (d) indicates decomposition: the melting points given are those obtained for the materials prepared as described: polymorphism may result in isolation of materials with different melting points in some preparations;

(vi) all final products were essentially pure by TLC and had satisfactory nuclear magnetic resonance (NMR) spectra and microanalytical data;

(vii) yields are given for illustration only;

(viii) when given, NMR data is in the form of delta values for major diagnostic protons, given in parts per million (ppm) relative to tetramethylsilane (TMS) as an internal standard, determined at 80 MHz, 250 MHz, 300 MHz or 400 MHz using $CDCl_3$, DMSO-$d_6$ or $CD_3OD$ as solvent: conventional abbreviations for signal shape are used, for example: s, singlet; d, doublet: m, multiplet: br, broad: etc.; in addition "Ar" signifies an aromatic group or signal;

(ix) reduced pressures are given as absolute pressures in pascals (Pa); other pressures are given as gauge pressures in bars;

(x) chemical symbols have their usual meanings: the following abbreviations have also been used: v (volume), w (weight); mp (melting point), l [liter(s)], ml (milliliters), g [gram(s)], mg [milligram(s)], min (minutes), h (hour); and (xi) solvent ratios are given in volume: volume (v/v) terms.

EXAMPLE 1

3-Methoxy-N-(2-methylphenylsulfonyl)-4-[1-propyl-5-(1-propyl-2-oxopyrrolidin-3-ylmethyl)indol-3-ylmethyl]benzamide a. Methyl 4-(5-cyanoindol-3-ylmethyl)-3-methoxybenzoate

A mixture of 5-cyanoindole (10 g) and freshly prepared silver carbonate on diatomaceous earth (40.66 g) was stirred and heated under reflux in toluene (100 ml) for 18 h, under an atmosphere of nitrogen. The mixture was cooled to room temperature, methyl 4-bromomethyl-3-methoxybenzoate (22.7 g) added, and stirring continued for 4 h. Ethyl acetate (200 ml) was added, the mixture filtered through diatomaceous earth, the filter pad washed with ethyl acetate and the filtrate evaporated. The dark oil obtained was purified by flash chromatography, eluting with 45:45:10 hexane:methylene chloride:ethyl acetate, to give a foam which was crystallized from toluene to give methyl 4-(5-cyanoindol-3-ylmethyl)-3-methoxybenzoate (11.8 g, 53%) as white crystals; mp 148–149°; partial NMR (250 MHz, DMSO-$d_6$): 3.83(s, 3H, OCH$_3$), 3.91(s, 3H, OCH$_3$), 4.08(s, 2H, ArCH$_2$Ar'), 8.00(s, 1H, H$^4$-indole), 11.49(br s, 1H, H$^1$-indole).

b. Methyl 4-(5-formylindol-3-ylmethyl)-3-methoxybenzoate

A solution of sodium hypophosphite monohydrate (24.8 g) in water (40 ml) was added to a solution of methyl 4-(5-cyanoindol-3-ylmethyl)-3-methoxybenzoate (11.33 g) in acetic acid (40 ml) and pyridine (80 ml). Raney nickel (approximately 2.5 g) was added as an aqueous slurry, and the mixture was heated at 50–55° for 3 h (CAUTION:evolution of hydrogen!). Ethyl acetate (200 ml) was added to the cooled solution, the mixture was filtered through diatomaceous earth, the filter pad washed with ethyl acetate, the combined filtrate washed with lM hydrochloric acid (4×200 ml, until the aqueous washings were acidic), water (2×100 ml) and brine, and dried (MgSO$_4$). The solvent was evaporated to give an oil which was purified by flash chromatography, eluting with 3:6:1 hexane: methylene chloride:ethyl acetate, giving a foam which was crystallized from a mixture of ethyl acetate and hexane to give methyl 4-(5-formylindol-3-ylmethyl)-3-methoxybenzoate (9.85 g, 86%) as white crystals; mp 117–120°; partial NMR (250 MHz, DMSO-$d_6$): 3.83(s, 3H, OCH$_3$); 3.94(s, 3H, OCH$_3$), 4.12(s, 2H, ArCH$_2$Ar'), 8.10(s, 1H, H$^4$-indole), 9.94(s, 1H, CHO), 11.45 (br s, 1H, H$^1$-indole).

c. Methyl 4-(5-formyl-1-propylindol-3-ylmethyl)-3-methoxybenzoate

Sodium hydride (2.96 g of a 60% w/w dispersion in mineral oil) was added to dry dimethylformamide (DMF, 100 ml), under a nitrogen atmosphere. The mixture was stirred and cooled in an ice-bath, and a solution of methyl 4-(5-formylindol-3-ylmethyl)-3-methoxybenzoate (20 g) in DMF (75 ml) added slowly. After 1 h, 1-bromopropane (9.13 g) was added slowly. After 2 h, the mixture was carefully acidified with 2M hydrochloric acid (100 ml), extracted with ethyl acetate (twice), and the extract washed with 1M hydrochloric acid, water, and brine. The dried (MgSO$_4$) solution was evaporated, and the residue dissolved in ethyl acetate and filtered through a pad of silica gel. The filtrate was evaporated, and the product crystallised from ether to give methyl 4-(5-formyl-1-propylindol-3-ylmethyl)-3-methoxybenzoate (19.2 g, 85%) as white needles; mp 98–99°; partial NMR (250 MHz, DMSO-$d_6$): 0.82(t, 3H, CH$_3$), 1.75(m, 2H, CH$_2$), 3.83(s, 3H, OCH$_3$), 3.92(s, 3H, OCH$_3$), 4.1(m, 4H, ArCH$_2$Ar' and NCH$_2$), 9.95(s, 1H, CHO).

d. Methyl 4-[5-[(hydroxy)(1-propyl-2-oxopyrrolidin-3-yl)methyl]-1-propylindol-3-ylmethyl]-3-methoxybenzoate A solution of 1-propyl-2-pyrrolindinone (0.834 g) in dry tetrahydrofuran (THF) (5 ml) was added to a stirred solution of lithium diisopropylamide [prepared from n-butyl lithium (6.57 mmol) and diisopropylamine (7.02 mmol)]in THF (15 ml) at −78° under a nitrogen atmosphere, and the mixture stirred at −78° for 1 h. The resulting solution was added to a solution of methyl 4-(5-formyl-1-propylindol-3-ylmethyl)-3-methoxybenzoate (2.0 g) in THF (15 ml) at −78°, under a nitrogen atmosphere. After 15 min at this temperature, the mixture was allowed to warm to ambient temperature over 1 h, then poured into 1M hydrochloric acid (50 ml) and extracted twice with ethyl acetate. The combined organic extract was washed (water, brine), dried (MgSO$_4$), and evaporated. The product was purified by flash chromatography, eluting with 3 2 methylene chloride:ethyl acetate, to give methyl 4-[5-[(hydroxy)(1-propyl-2-oxopyrrolidin-3-yl)methyl]-1-propylindol-3-ylmethyl]-3-methoxy benzoate (1.38 g, 51%, as a separable mixture of diastereomers) as an oil; isomer A partial NMR (300 MHz, DMSO-$d_6$): 0.67(t, 3H, CH$_3$), 0.80(t, 3H, CH$_3$), 3.83(s, 3H, OCH$_3$), 3.93(s, 3H, OCH$_3$), 4.92(d, 1H, CHOH), 5.48(br s, about 1H, CHOH); isomer B partial NMR (400 MHz, DMSO-$d_6$): 0.80(m, 6H, 2xCH$_3$), 3.82(s, 3H, OCH$_3$), 3.91(s, 3H, OCH$_3$), 5.13(br s, 1H, CHOH), 5.25(br s, 1H, CHOH).

e. Methyl 4-[5-[(acetoxy)(1-propyl-2-oxopyrrolidin-3-yl)methyl]-1-propylindol-3-ylmethyl]-3-methoxybenzoate Acetic anhydride (2.6 g) and triethylamine (0.26 g) were added to a solution of methyl 4-[5-[(hydroxy)(1-propyl-2-oxopyrrolindin-3-yl)methyl]-1-propylindol-3-ylmethyl]-3-methoxybenzoate (0.64 g) in methylene chloride (20 ml), and the mixture stirred and heated under reflux for 4 days. The solvent was evaporated, and the product purified by flash chromatography, eluting with 35:35:30 hexane:methylene chloride:ethyl acetate, to give methyl 4-[5-[(acetoxy)-(1-propyl-2-oxopyrrolidin-3-yl)methyl]-1-propylindol-3-ylmethyl]-3-methoxy benzoate (1.27 g, 90%, as a separable mixture of diastereomers) as an oil: isomer A partial NMR (400 MHz, DMSO-$d_6$) 0.65(t, 3H, CH$_3$), 0.80(t, 3H, CH$_3$), 2.02(s, 3H, OCOCH$_3$), 3.83(s, 3H, OCH$_3$), 3.92(s, 3H, OCH$_3$), 6.06(d, 2H, CHOCOCH$_3$); isomer B partial NMR (400 MHz, DMSO-$d_6$): 0.81(t, 6H, 2xCH$_3$), 1.98(s, 3H, OCOCH$_3$), 3.83(s, 3H, OCH$_3$), 3.90(s, 3H, OCH$_3$), 6.12(d, 1H, CHOCOCH$_3$).

f. Methyl 3-methoxy-4-[1-propyl-5-(1-propyl-2-oxopyrrolindin-3-ylmethyl)indol-3-ylmethyl]-benzoate Palladium on carbon (10% w/w, 0.8 g) and ammonium formate (1.23 g) were added to a degassed (with nitrogen) solution of methyl 4-[5-[(acetoxy) -(1-propyl-2-oxopyrrolindin-3-yl)methyl]-1-propylindol -3-ylmethyl]-3-methoxybenzoate (1.23 g) in methanol (30 ml). The mixture was stirred and heated at 55° .for 30 min. Ethyl acetate (50 ml) was added to the cooled mixture, which was filtered through diatomaceous earth and evaporated. The product was purified by flash chromatography, eluting with 1:1 ethyl acetate:hexane, to give methyl 3-methoxy-4-[1-propylylmethyl -5-(1-propyl-2-oxopyrrolidin-3-ylmethyl)indol-3-ylmethyl]benzoate (0.9 g, 82%) as an oil; partial NMR (400 MHz, DMSO-$d_6$): 0.80(m, 6H, 2xCH$_3$), 3.82 (s, 3H, OCH$_3$), 3.91(s, 3H, OCH$_3$).

g. 3-Methoxy-4-[1-propyl-5-(1-propyl-2-oxopyrrolidin -3-ylmethyl)indol-3-ylmethyl]benzoic acid A solution of lithium hydroxide monohydrate (0.044 g) in water (3 ml) was added to a stirred solution of methyl 3-methoxy-4-[1-propyl-5-(1-propyl -2-oxopyrrolindin-3-ylmethyl)indol-3-ylmethyl]benzoate under a nitrogen atmosphere. After 18 h, the organic solvent was evaporated, and the resulting aqueous solution acidified with 1M hydrochloric acid. The precipitate was collected and washed with water to give 3-methoxy-4-[1-propyl-5-(1-propyl-2-oxopyrrolidin -3-ylmethyl)indol-3-ylmethyl]benzoic acid (0.78 g, 89%) as an off-white solid; mp 75–86°.

Analysis for $C_{28}H_{34}N_2O_4.0.25\ H_2O$:
Calculated: C, 72.00; H, 7.44; N, 5.99.
Found: C, 72.03; H, 7.33; N, 5.96.

h. 3-Methoxy-N-(2-methylphenylsulfonyl)-4-[1-propyl -5-(1-propyl-2-oxopyrrolidin-3-ylmethy)indol -3-ylmethyl]benzamide A mixture of 3-methoxy-4-[1-propyl-5-(1-propyl-2-oxopyrrolidin-3-ylmethyl)indol-3-ylmethyl]-benzoic acid (0.3 g), 4-dimethylaminopyridine (0.095 g), 1-(3-dimethylaminopropyl)-3-ethylcarbodiimide hydrochloride (0.149 g), and 2-methylbenzenesulfonamide (0.122 g) was dissolved in methylene chloride (10 ml), and the solution was stirred under a nitrogen atmosphere for 18 h. The mixture was poured into 1M hydrochloric acid, extracted with ethyl acetate (twice), and the extract washed with 1M hydrochloric acid, water, and brine. The dried (MgSO$_4$) solution was evaporated and the residue precipitated from a mixture of methanol and 1M hydrochloric acid to give 3-methoxy-N-(2-methylphenylsulfonyl)-4-[1-propyl-5-(1-propyl-2-oxopyrrolidin-3-ylmethyl)indol-3-ylmethyl]-benzamide (0.38 g, 95%) as an off-white solid; mp 98–115°.

Analysis for $C_{35}H_{41}N_3O_5S$:
Calculated: C, 68.26; H, 6.71; N, 6.82.

Found: C, 67.89; H, 6.72; N, 6.65.
The methyl 4-bromomethyl-3-methoxybenzoate used in part a., above, was prepared as follows:

i. Methyl 3-methoxy-4-methylbenzoate

A solution of 3-methoxy-4-methylbenzoic acid (6.0 g) in methanol (120 ml) was treated with acetyl chloride (6 ml) and stirred for 36 hours. The solution was evaporated. The residue was dissolved in methanol (100 ml) and the solution evaporated. This procedure was repeated to give methyl 3-methoxy-4-methylbenzoate (6.34 g, 98%) as a colorless oil; NMR (80 MHz, CDCl$_3$) 2.2(s, 3H, CH$_3$), 3.9(2s, 6H, 2 x OCH$_3$), 7.1(d, 1H), 7.5(m, 2H).

j. Methyl 4-bromomethyl-3-methoxybenzoate

A stirred solution of methyl 3-methoxy -4-methylbenzoate (121.2 g) in carbon tetrachloride (1.4 liter) was heated under gentle reflux with a 350 watt tungsten lamp and subjected to an air purge by means of a T-tube attached to a water aspirator. A solution of bromine (107.2 g) in carbon tetrachloride (500 ml) was added dropwise over 4 hr. Evaporation of the solvent gave a light yellow solid which was triturated with 500 ml of 1:9 ether:hexane. The solid was collected by filtration to give methyl 4-bromomethyl -3-methoxybenzoate (111.7 g, 64%) as a pale yellow solid: mp 87–90°; NMR (80 MHz, CDCl$_3$): 3.9(2s, 6H, 2 x OCH$_3$), 4.5(s, 2H, BrCH$_2$), 7.4(m, 3H).

The 1-propyl-2-pyrrolidinone used in part d., above, was prepared as follows:

k. 1-Propyl-2-pyrrolidinone

2-Pyrrolidinone (2.0 g) was added slowly to a stirred suspension of sodium hydride (0.94 g of a 60% dispersion in mineral oil, washed free of the oil by washing with hexane) in dry N, N-dimethylforramide (20 ml) cooled in an ice-bath under a nitrogen atmosphere. The mixture was stirred at ice-bath temperature for 30 min, then at ambient temperature for 1 hr. 1-bromopropane (2.88 g) was added dropwise, the mixture stirred at ambient temperature for 15 hr, then diluted with ethyl acetate (100 ml), washed with water (4×50 ml), brine, dried and evaporated to give an oil. The product was purified by distillation (98° @ 10 mm Hg, bulb-to-bulb) to give N-propyl-2-pyrrolidinone (1.2 g, 41%) as a colorless oil: NMR (250 MHz, DMSO-$d_6$): 0.81(t, 3H, Me), 1.45(m, 2H, CH$_2$), 1.91(m, 2H, CH$_2$), 2.22(t, 2H, CH$_2$), 3.11(t, 2H, CH$_2$), 3.30(t, 2H, CH$_2$).

EXAMPLES 2–3

Using a similar procedure to that described in Example 1.h., except starting from the appropriate sulfonamides of formula $R^{12}$SO$_2$NH$_2$, the following compounds of formula Ib, Q=0, n=1, m=1, $R^3$=H, $R^1$=$R^9$=n -CH$_3$H$_7$, $R^{11}$=OCH$_3$, were prepared, all obtained as solids:

| Example | $R^{12}$ | mp | Analysis | Yield |
| --- | --- | --- | --- | --- |
| 2 | 2-bromophenyl | 103–112° | for $C_{34}H_{38}BrN_3O_5S$<br>Calc'd: C, 59.99; H, 5.62; N, 6.17<br>Found: C, 59.71; H, 5.64; N, 6.16 | 99% |
| 3 | 2-chlorophenyl | 110–121° | for $C_{34}H_{38}ClN_3O_5S.0.25\ H_2O$<br>Calc'd: C, 63.74; H, 6.05; N, 6.56<br>Found: C, 63.74; H, 6.02; N, 6.96 | 91% |

EXAMPLE 4

3-Methoxy-4-[1-methyl-5-(1-methyl-2-oxopyrrolidin-3-ylmethyl)indol-3-ylmethyl]-N-(2-methylphenylsulfonyl)benzamide a. Methyl 4-(5-formyl-1-methylindol-3-ylmethyl)-3-methoxybenzoate

Sodium hydride (1.23 g of a 60% dispersion in mineral oil) was added to dry N,N-dimethylformamide (100 ml), under an atmosphere of nitrogen. The mixture was cooled in an ice-bath, a solution of methyl 4-(5-formylindol-3-ylmethyl)-3-methoxybenzoate (9.0 g) in N,N-dimethylformamide (20 ml) added slowly, and the mixture stirred for 1 hr. Methyl iodide (4.34 g) was added slowly, stirring continued for 2.5 hr., then the mixture carefully acidified with hydrochloric acid (100 ml) to give an off-white precipitate which was purified by flash chromatography, eluting with 45:50:5 hexane:methylene chloride:ethyl acetate, to give a yellow oil which was crystallized from a mixture of ethyl acetate and hexane to give methyl 4-(5-formyl-1-methylindol-3-ylmethyl)-3-methoxybenzoate (81%) as an off-white powder; mp 116–118 C°; partial NMR(250 MHz, DMSO-$d_6$): 3.80 (s, 3H, OCH$_3$), 3.83(s, 3H, NCH$_3$), 3.93(s, 3H, OCH$_3$), 4.11(s, 2H, ArCH$_2$Ar'), 8.12(s, 1H, H4-indole), 9.96 (s, 1H, CHO).

b. Methyl 4-[5-[(hydroxy)(1-methyl-2-oxopyrrolidin-3-yl)methyl]-1-methylindol-3-ylmethyl]-3-methoxybenzoate Using a similar procedure to that described in Example 1, part d, except starting from methyl 4-(5-formyl-1-methylindol-3-ylmethyl)-3-methoxybenzoate and N-methylpyrrolidone, methyl 4-[5-[(hydroxy)-(1-methyl-2-oxopyrrolidin-3-yl)methyl]-1-methylindol-3-ylmethyl]-3-methoxybenzoate was obtained (40%) as a foam; NMR (300 MHz, DMSO-$d_6$): 1.43–1.65 (m, 1.5H), 1.95 (m, 0.5H), 2.40–2.60 (m, 2.5H), 2.65–2.80 (m, 2H), 2.90–3.25 (m, 1.5H), 3.70 (s, 3H), 3.83 (s, 3H), 3.85–4.08 (m, 5H), 4.92 (d, 0.5H), 5.17 (s, 0.5H), 7.0–7.55 (m, 7H).

c. Methyl 4-[5-[(acetoxy)(1-methyl-2-oxopyrrolidin-3-yl)methyl]-1-methylindol-3-ylmethyl]-3-methoxybenzoate Using a similar procedure to that described in Example 1, part e, except starting from methyl 4-[5-[(hydroxy)(1-methyl-2-oxopyrrolidin-3-yl)methyl]-1-methylindol-3-ylmethyl]-3-methoxybenzoate, methyl 4-[5-[(acetoxy)(1-methyl-2-oxopyrrolidin-3-yl)methyl]-1-methylindol-3-ylmethyl]-3-methoxybenzoate was obtained (95%) as an oil: partial NMR (300 MHz, DMSO-$d_6$) 1.50–2.10 (m, 5H), 2.5–3.3 (m, 6H), 3.71 (s, 3H, CH$_3$), 3.83 (s, 3H, OCH$_3$), 3.85–4.10 (m, 5H).

d. Methyl 3-methoxy-4-[1-methyl-5-(1-methyl-2-oxopyrrolidin-3-ylmethyl)indol-3-ylmethyl]benzoate Using a similar procedure to that described in Example 1, part f, except starting from methyl 4-[5-[(acetoxy)(1-methyl-2-oxopyrrolidin-3-yl)methyl]-1-methylindol-3-ylmethyl]-3-methoxybenzoate, methyl 3-methoxy-4-[1-methyl-5-(1-methyl-2-oxopyrrolidin-3-ylmethyl)indol-3-ylmethyl]benzoate was obtained (65%) as an oil: partial NMR (300 MHz, DMSO-$d_6$): 1.50–1.65 (m, 1H), 1.78–1.92 (m, 1H), 2.51–2.70 (m, 5H), 2.95–3.20 (m, 3H), 3.69 (s, 3H, CH$_3$), 3.83 (s, 3H, OCH$_3$), 3.92 (s, 3H, OCH$_3$), 4.00 (s, 2H).

e. 3-Methoxy-4-[1-methyl-5-(1-methyl-2-oxopyrrolidin-3-ylmethyl)indol-3-ylmethyl]benzoic acid Using a similar procedure to that described in Example 1, part g, except starting from methyl 3-methoxy-4-[1-methyl-5-(1-methyl-2-oxopyrrolidin-3-ylmethyl)indol-3-ylmethyl]benzoate, 3-methoxy-4-[1-methyl-5-(1-methyl-2-oxopyrrolidin-3-ylmethyl)indol-3-ylmethyl]benzoic acid was obtained (72%) as a white solid; mp 232–233° C.

f. 3-Methoxy-4-[1-methyl-5-(1-methyl-2-oxopyrrolidin-3-ylmethyl)indol-3-ylmethyl]-N-(2-methylphenylsulfonyl)benzamide Using a similar procedure to that described in Example 1, part h, except starting from 3-methoxy-4-[1-methyl-5-(1-methyl-2-oxopyrrolidin-3-ylmethyl)indol-3-ylmethyl]benzoic acid, the title compound was obtained (79%) as a white solid: mp 115–135° C.

Analysis for $C_{31}H_{33}N_3O_5S$:
Calculated: C, 66.53; H, 5.94; N, 7.51.
Found: C, 66.46; H, 6.02; N, 7.58.

EXAMPLE 5

N-(2-Chlorophenylsulfonyl)-3-methoxy-4-[1-methyl-5-(1-methyl-2-oxopyrrolidin-3-ylmethyl)indol-3-ylmethyl]benzamide Using a similar procedure to that described in Example 4, part f, except using 2-chlorophenylsulfonamide instead of 2-methylphenylsulfonamide, the title compound was obtained (82%) as a white solid; mp 128–135° C.

Analysis for $C_{30}H_{30}ClN_3O_5S$:
Calculated: C, 62.12; H, 5.21; N, 7.24.
Found: C, 61.95; H, 5.29; N, 7.24.

EXAMPLE 6

4-[2-Chloro-1-methyl-5-(1-methyl-2-oxopyrrolidin-3-ylmethyl)indol-3-ylmethyl]-3-methoxy-N-(2-methylphenylsulfonyl)benzamide a. Methyl 4-[2-chloro-1-methyl-5-(1-methyl-2-oxopyrrolidin-3-ylmethyl)indol-3-ylmethyl]-3-methoxybenzoate N-Chlorosuccinimide (0.282 mg) was added in one portion to a stirred solution of methyl 4-[1-methyl-5-(1-methyl-2-oxopyrrolidin-3-ylmethyl)indol-3-ylmethyl]-3-methoxybenzoate (0.9 g) in dry dichloromethane (20 ml), under a nitrogen atmosphere. After 15 minutes, the solvent was evaporated, and the product was purified by flash chromatography, eluting with ethyl acetate, to give methyl 4-[2-chloro-1-methyl-5-(1-methyl-2-oxopyrrolidin-3-ylmethyl)indol-3-ylmethyl](65%) as a yellow oil: NMR (300 MHz, DMSO-$d_6$): 1.45–1.61 (m, 1H), 1.75–1.90 (m, 1H), 2.50–2.70 (m, 5H), 2.90–3.18 (m, 3H), 3.72 (s, 3H, CH$_3$), 3.82 (s, 3H, CH$_3$), 3.92 (s, 3H, CH$_3$), 4.02 (s, 2H), 6.99–7.10 (m, 2H), 7.20 (s, 1), 7.38 (d, 1H), 7.40–7.50 (m, 2H).

b. 4-[2-Chloro-1-methyl-5-(1-methyl-2-oxopyrrolidin-3-ylmethyl)indol-3-ylmethyl]-3-methoxybenzoic acid Using a similar procedure to that described in Example 1, part g, except starting from methyl 4-[2-chloro-1-methyl-5-(1-methyl-2-oxopyrrolidin-3-ylmethyl)indol-3-ylmethyl]-3-methoxybenzoate, 4-[2-chloro-1-methyl-5-(1-methyl-2-oxopyrrolidin-3-ylmethyl)-indol-3-ylmethyl]-3-methoxybenzoic acid was obtained (83%) as a white solid; mp 204–205° C.

c. 4-[2-Chloro-1-methyl-5-(1-methyl-2-oxopyrrolidin-3-ylmethyl)indol-3-ylmethyl]-3-methoxy-N-(2-methylphenylsulfonyl)benzamide Using a similar procedure to that described in Example 1, part h, except starting from 4-[2-chloro-1-methyl-5-(1-methyl-2-oxopyrrolidin-3-ylmethyl)indol-3-ylmethyl]-3-methoxybenzoic acid, the title compound was obtained (92%) as a white solid: mp 129–133° C.

Analysis for $C_{31}H_{32}ClN_3O_5S$:
Calculated: C, 62.11; H, 5.48; N, 7.01.
Found: C, 62.16; H, 5.48; N, 6.90.

EXAMPLE 7

4-[2-Chloro-1-methyl-5-(1-methyl-2-oxopyrrolidin-3-ylmethyl)indol-3-ylmethyl]-N-(2-chlorophenylsulfonyl)-3-methoxybenzamide Using a similar procedure to that described in Example 6, part c, except using 2-chlorophenylsulfonamide instead of 2-methylphenylsulfonamide, the title compound was obtained (89%) as a white solid; mp 126–134° C.

Analysis for $C_{30}H_{29}Cl_2N_3O_5S \cdot 0.5\ H_2O$
Calculated: C, 57.79; H, 4.85; N, 6.74.
Found: C, 57.73; H, 4.75; N, 6.62.

EXAMPLE 8

3-Methoxy-4-[5-(1-methyl-2-oxopyrrolidin-3-ylmethyl)-1-propylindol-3-ylmethyl]-N-(2-methylphenylsulfonyl)benzamide a. Methyl 4-[5-[(hydroxy)(1-methyl-2-oxopyrrolidin-3-yl)methyl]-1-propylindol-3-ylmethyl]-3-methoxybenzoate Using a similar procedure to that described in Example 1, part d, except using N-methylpyrrolidone instead of N-propylpyrrolidone, methyl 4-[5-[(hydroxy)(1-methyl-2-oxopyrrolidin-3-yl)methyl]-1-propylindol-3-ylmethyl]-3-methoxybenzoate was obtained (32%) as a separable pair of diastereomers, as a foam; isomer A partial NMR (300 MHz, DMSO-$d_6$) 0.80 (t, 3H, CH$_3$), 1.50–1.75 (m, 4H), 2.53 (s, 3H, CH$_3$), 3.82 (s, 3H, OCH$_3$), 3.92 (s, 3H, OCH$_3$), 4.90 (d, 1H, CHOH); isomer B partial NMR (300 MHz, DMSO-$d_6$): 0.80 (t, 3H, CH$_3$), 2.73 (s, 3H, CH$_3$), 3.83 (s, 3H, OCH$_3$), 3.91(s, 3H, OCH$_3$), 5.13 (br d, 1H, CHOH).

b. Methyl 4-[5-[(acetoxy)(1-methyl-2-oxopyrrolidin-3-yl)methyl]-1-propylindol-3-ylmethyl]-3-methoxybenzoate Using a similar procedure to that described in Example 1, part e, except using methyl 4-[5-[(hydroxy)(1-methyl-2-oxopyrrolidin-3-yl)methyl]-1-propylindol-3-ylmethyl]-3-methoxybenzoate, methyl 4-[5-[(acetoxy)(1-methyl-2-oxopyrrolidin-3-yl)methyl]-1-propylindol-3-ylmethyl]-3-methoxybenzoate was obtained (76%) as a separable mixture of diastereomers, as a foam; isomer A partial NMR (300 MHz, DMSO-$d_6$): 0.80 (t, 3H, CH$_3$), 2.02 (s, 3H, COCH$_3$), 2.53 (s, 3H, CH$_3$), 3.83 (s, 3H, OCH$_3$), 3.92 (s, 3H, OCH$_3$), 6.04 (d, 1H, CHOCOCH$_3$) isomer B partial NMR (300 MHz, DMSO-$d_6$) 0.81 (t, 3H, CH$_3$), 1.99 (s, 3H, COCH$_3$), 2.73 (s, 3H, CH$_3$), 3.83 (s, 3H, OCH$_3$), 3.90 (s, 3H, OCH$_3$), 6.10 (d, 1H, CHOCOCH$_3$).

c. Methyl 3-methoxy-4-[5-(1-methyl-2-oxopyrrolidin-3-ylmethyl)-1-propylindol-3-ylmethyl]benzoate Using a similar procedure to that described in Example 1, part f, except using methyl 4-[5-[(acetoxy)(1-methyl-2-oxopyrrolidin-3-yl)methyl]-1-propylindol-3-ylmethyl]-3-methoxybenzoate, methyl 3-methoxy-4-[5-(1-methyl-2-oxopyrrolidin-3-ylmethyl)-1-propylindol-3-ylmethyl]benzoate was obtained (75%) as an oil: partial NMR (300 MHz, DMSO-$d_6$) 0.81 (t, 3H, CH$_3$), 2.67 (s, 3H, CH$_3$), 3.83 (s, 3H, OCH$_3$), 3.91 (s, 3H, OCH$_3$), 4.0–4.10 (m, 4H).

d. 3-Methoxy-4-[5-(1-methyl-2-oxopyrrolidin-3-ylmethyl)-1-propylindol-3-ylmethyl]benzoic acid Using a similar procedure to that described in Example 1, part g, except using methyl 3-methoxy-4-[5-(1-methyl-2-oxopyrrolidin-3-ylmethyl)-1-propyl-indol-3-ylmethyl]benzoate, 3-methoxy-4-[5-(1-methyl-2-oxopyrrolidin-3-ylmethyl)-1-propylindol-3-ylmethyl]benzoic acid was obtained (83%) as a solid; mp 98–107° C.

e. 3-Methoxy-4-[5-(1-methyl-2-oxopyrrolidin-3-ylmethyl)-1-propylindol-3-ylmethyl]-N-(2-methylphenylsulfonyl)benzamide Using a similar procedure to that described in Example 1, part h, the title compound was obtained (91%) as a solid; mp 103–115° C.

Analysis for $C_{33}H_{37}N_3O_5S \cdot 0.25\ H_2O$:
Calculated: C, 66.93; H, 6.38; N, 7.09.
Found: C, 66.97; H, 6.36; N, 6.99.

EXAMPLE 9

3-Methoxy-4-[5-(1-methyl-2-oxopiperidin-3-ylmethyl)-1-propylindol-3-ylmethyl]-N-(2-methylphenylsulfonyl)benzamide a. Methyl 4-[5-[(hydroxy)(1-methyl-2-oxopiperidin-3-yl)methyl]-1-propylindol-3-ylmethyl]-3-methoxybenzoate Using a similar procedure to that described in Example 1, part d, except using N-methylpiperidone instead of N-propylpyrrolidone, methyl 4-]5-[(hydroxy)(1-methyl-2-oxopiperidin-3-yl)methyl]-1-propylindol-3-ylmethyl]-3-methoxybenzoate was obtained (40%) as a separable mixture of diastereomers, as a foam; isomer A, partial NMR (300 MHz, DMSO-$d_6$): 0.82 (t, 3H, CH$_3$), 2.78 (s, 3H, CH$_3$), 3.83 (s, 3H, OCH$_3$), 3.91 (s, 3H, OCH$_3$), 4.94 (d, 1H, CHOH); isomer B, partial NMR (300 MHz, DMSO-$d_6$): 0.81 (t, 3H, CH$_3$), 2.83 (s, 3H, CH$_3$), 3.83 (s, 3H, OCH$_3$), 3.91 (s, 3H, OCH$_3$), 5.44 (d, 1H, CHOH).

b. Methyl 4-[5-[(acetoxy)(1-methyl-2-oxopiperidin-3-yl)methyl]-1-propylindol-3-ylmethyl]-3-methoxybenzoate Using a similar procedure to that described in Example 1, part e, except using methyl 4-[5-[(hydroxy)(1-methyl-2-oxopiperidin-3-yl)methyl]-1-propylindol-3-ylmethyl]-3-methoxybenzoate, methyl 4-[5-[(acetoxy)(1-methyl-2-oxopiperidin-3-yl)methyl]-1-propylindol-3-ylmethyl]-3-methoxybenzoate was obtained (72%) as a separable mixture of diastereomers, as an oil; isomer A, partial NMR (300 MHz, DMSO-$d_6$): 0.82 (t, 3H, CH$_3$), 2.02 (s, 3H, COCH$_3$), 2.67 (s, 3H, CH$_3$), 3.83 (s, 3H, OCH$_3$), 3.91 (s, 3H, OCH$_3$), 6.44 (d, 1H, CHO- COCH₃): isomer B, partial NMR (300 MHz, DMSO-d₆): 0.82 (t, 3H, CH₃), 1.98 (s, 3H, COCH₃), 2.84 (s, 3H, CH₃), 3.83 (s, 3H, OCH₃), 3.90 (s, 3H, OCH₃), 6.46 (d, 1H, CHOCOCH₃)

c. Methyl 3-methoxy-4-[5-(1-methyl-2-oxopiperidin-3-ylmethyl)-1-propylindol-3-ylmethyl]benzoate Using a similar procedure to that described in Example 1, part f, except starting from methyl 4-[5-[(acetoxy)(1-methyl-2-oxopiperidin-3-yl)methyl]-1-propylindol-3-ylmethyl]-3-methoxybenzoate, methyl 3-methoxy-4-[5-(1-methyl-2-oxopiperidin -3-ylmethyl)-1-propylindol-3-ylmethyl]benzoate was obtained (77%) as an oil; partial NMR (300 MHz, DMSO-d₆) 0.82 (t, 3H, CH₃), 2.80 (s, 3H, CH₃), 3.83 (s, 3H, OCH₃), 3.91 (s, 3H, OCH₃), 4.0 (m, 4H).

d. 3-Methoxy-4-[5-(1-methyl-2-oxopiperidin-3-ylmethyl)-1-propylindol-3-ylmethyl]benzoic acid Using a similar procedure to that described in Example 1, part g, except starting from methyl 3-methoxy-4-[5-(1-methyl-2-oxopiperidin-3-ylmethyl)-1-propylindol-3-ylmethyl]benzoate, 3-methoxy-4-[5-(1-methyl-2-oxopiperidin-3-ylmethyl)-1-propylindol -3-ylmethyl]benzoic acid was obtained (95%) as a solid; mp 105–115° C.

e. 3-Methoxy-4-[5-(1-methyl-2-oxopiperidin-3-ylmethyl)-1-propylindol-3-ylmethyl]-N-(2-methylphenylsulfonyl)benzamide Using a similar procedure to that described in Example 1, part h, except starting from 3-methoxy -4-[5-(1-methyl-2-oxopiperidin-3-ylmethyl)-1-propylindol -3-ylmethyl]benzoic acid, the title compound was obtained (88%) as a solid; mp 120–128° C.

Analysis for C₃₄H₃₉N₃O₅S:
Calculated: C, 67.86; H, 6.53; N, 6.98.
Found: C, 67.73; H, 6.61; N, 6.83.

EXAMPLE 10

4-[5-(1-Ethyl-2-oxopyrrolidin-3-ylmethyl)-1-propylindol -3-ylmethyl]-3-methoxy-N-(2-methylphenylsulfonyl)-benzamide a. Methyl 4-[5-[(hydroxy)(1-ethyl-2-oxopyrrolidin-3-yl)methyl]-1-propylindol-3-ylmethyl]-3-methoxybenzoate Using a similar procedure to that described in Example 1, part d, except using N-ethylpyrrolidone instead of N-propylpyrrolidone, methyl 4-[5-[(hydroxy) (1-ethyl-2-oxopyrrolidin-3-yl)methyl]-1-propylindol -3-ylmethyl]-3-methoxybenzoate was obtained (63%) as an inseparable mixture of diastereomers, as an oil; partial NMR (300 MHz, DMSO-d₆): 0.75–1.04 (m, 6H, CH₃), 3.83 (s, 3H, OCH₃), 3.91 (s, 1.5H, OCH₃), 3.92 (s, 1.5H, OCH₃), 4.91 (d, 0.5H, CHOH), 5.13 (br s, 0.5H, CHOH).

b. Methyl 4-[5-[(acetoxy)(1-ethyl-2-oxopyrrolidin-3-yl)methyl]-1-propylindol-3-ylmethyl]-3-methoxybenzoate Using a similar procedure to that described in Example 1, part e, except starting from methyl 4-[5 -[(hydroxy)(1-ethyl-2-oxopyrrolidin-3-yl)methyl]-1-propylindol-3-ylmethyl]-3-methoxybenzoate, methyl 4-[5-[(acetoxy)(1-ethyl-2-oxopyrrolidin-3-yl)methyl]-1-propylindol-3-ylmethyl]-3-methoxybenzoate was obtained (quantitative yield) as an inseparable mixture of diastereomers, as an oil; partial NMR (300 MHz, DMSO-d₆): 0.75–1.03 (m, 6H, CH₃), 1.99 (s, 1.5H, COCH₃), 2.02 (s, 1.5H, COCH₃), 3.83 (s, 3H, OCH₃), 3.90 (s, 1.5H, OCH₃), 3.92 (s, 1.5H, OCH₃), 6.05 (d, 0.5H, CHOCOCH₃), 6.11 (d, 0.5H, CHOCOCH₃).

c. Methyl 4-[5-(1-ethyl-2-oxopyrrolidin-3-ylmethyl)-1-propylindol-3-ylmethyl]-3-methoxybenzoate Using a similar procedure to that described in Example 1, part f, except starting from methyl 4-[5-[(acetoxy)(1-ethyl-2-oxopyrrolidin-3-yl)methyl]-1-propylindol-3-ylmethyl]-3-methoxybenzoate, methyl 4-[5-(1-ethyl-2-oxopyrroli-din-3-ylmethyl)-1-propylindol -3-ylmethyl]-3-methoxybenzoate was obtained (81%) as an oil; partial NMR (300 MHz, DMSO-d₆): 0.80 (t, 3H, CH₃), 0.95 (t, 3H, CH₃), 3.83 (s, 3H, OCH₃), 3.91 (s, 3H, OCH₃), 4.00–4.05 (m, 4H).

d. 4-[5-(1-Ethyl-2-oxopyrrolidin-3-ylmethyl)-1-propylindol-3-ylmethyl]-3-methoxybenzoic acid Using a similar procedure to that described in Example 1, part g, except starting from methyl 4-[5-(1-ethyl-2-oxopyrrolidin-3-ylmethyl)-1-propylindol-3-ylmethyl]-3-methoxybenzoate, 4-[5-(1-ethyl-2-oxopyrrolidin -3-ylmethyl)-1-propylindol-3-ylmethyl]-3-methoxybenzoic acid was obtained (88%) as a solid; mp 94–99° C.

e. 4-[5-(1-Ethyl-2-oxopyrrolidin-3-ylmethyl)-1-propylindol-3-ylmethyl]-3-methoxy-N-(2-methylphenylsulfonyl)benzamide Using a similar procedure to that described in Example 1, part h, except using 4-[5-(1-ethyl-2-oxopyrrolidin-3-ylmethyl)-1-propylindol-3-ylmethyl]-3-methoxybenzoic acid, the title compound was obtained (91%) as a solid: mp 107–115° C.

Analysis for C 0.2 H2O:
Calculated: C, 67.46: H, 6.55; N, 6.94.
Found: C, 67.43, H, 6.50; N, 6.86.

EXAMPLE 11

3-Methoxy-N-(2-methylphenylsulfonyl)-4-[1-methyl -5-(1-propyl-2-oxopyrrolidin-3-ylmethyl)indol-3-ylmethyl]benzamide a. Methyl 4-[5-[(hydroxy)(1-propyl-2-oxopyrrolidin -3-yl)methyl]-1-methylindol-3-ylmethyl]-3-methoxybenzoate Using a similar procedure to that described in Example 1, part d, except using methyl 4-(5-formyl -1-methylindol-3-ylmethyl)-3-methoxybenzoate, methyl 4-[5-[(hydroxy)(1-propyl-2-oxopyrrolidin-3-yl)methyl]-1-methylindol-3-ylmethyl]-3-methoxybenzoate was obtained (37%) as an oil; partial NMR (300 MHz, DMSO-d₆) 0.69 (t, 1.5H, CH₃), 0.82 (t, 3H, CH₃), 3.70 (s, 3H, CH₃), 3.83 (s, 3H, OCH₃), 3.91 (s, 1.5H, OCH₃), 3.92 (s, 1.5H, OCH₃).

b. Methyl 4-[5-[(acetoxy)(1-propyl-2-oxopyrrolidin -3-yl)methyl]-1-methylindol-3-ylmethyl]-3-methoxybenzoate Using a similar procedure to that described in Example 1, part e, except starting from methyl 4-[5-[(hydroxy)(1-propyl-2-oxopyrrolidin-3-yl)methyl]-1-methylindol-3-ylmethyl]-3-methoxybenzoate, methyl 4-[5-[(acetoxy)(1-propyl-2-oxopyrrolidin-3-yl)methyl]-1-methylindol-3-ylmethyl]-3-methoxybenzoate was obtained (quantitative yield) as an oil; partial NMR (300 MHz, DMSO-$d_6$) 0.67 (t, 1.5H, $CH_3$), 0.82 (t, 1.5H, $CH_3$), 1.99 (s, 1.5H, $COCH_3$), 2.08 (s, 1.5H, $COCH_3$), 3.71 (s, 3H, $CH_3$), 3.81 (s, 3H, $OCH_3$), 3.91 (s, 1.5H, $OCH_3$), 3.93 (s, 1.5H, $OCH_3$), 6.09 (d, 0.5H, C$\underline{H}$O-$COCH_3$), 6.13 (d, 0.5H, C$\underline{H}$O$COCH_3$).

c. Methyl 3-methoxy-4-[1-methyl-5-(1-propyl-2-oxopyrrolidin-3-ylmethyl)indol-3-ylmethyl]benzoate Using a similar procedure to that described in Example 1 part f, except starting from methyl 4-[5-[(acetoxy)(1-propyl-2-oxopyrrolidin-3-yl)methyl]-1-methylindol-3-ylmethyl]-3-methoxybenzoate, methyl 3-methoxy-4-[1-methyl-5-(1-propyl-2-oxopyrrolidin-3-ylmethyl)indol-3-ylmethyl]benzoate was obtained (66%) as an oil; partial NMR (300 MHz, DMSO-$d_6$) 0.78 (t, 3H, $CH_3$), 1.40 (m, 2H, $CH_2CH_3$), 3.69 (s, 3H, $CH_3$), 3.83 (s, 3H, $OCH_3$), 3.91 (s, 3H, $OCH_3$), 3.99 (s, 2H).

d. 3-Methoxy-4-[1-methyl-5-(1-propyl-2-oxopyrrolidin-3-ylmethyl)indol-3-ylmethyl]benzoic acid Using a similar procedure to that described in Example 1, part g, except starting from methyl 3-methoxy-4-[1-methyl-5-(1-propyl-2-oxopyrrolidin-3-ylmethyl)indol-3-ylmethyl]benzoate, 3-methoxy-4-[1-methyl-5-(1-propyl-2-oxopyrrolidin-3-ylmethyl) indol-3-ylmethyl]benzoic acid was obtained (86%) as a solid: mp 202–212° C.

e. 3-Methoxy-N-(2-methylphenylsulfonyl)-4-[1-methyl-5-(1-propyl-2-oxopyrrolidin-3-ylmethyl)indol-3-ylmethyl]benzamide Using a similar procedure to that described in Example 1, part h, except starting from 3-methoxy-4-[1-methyl-5-(1- propyl-2-oxopyrrolidin-3-ylmethyl) indol-3-ylmethyl]benzoic acid, the title compound was obtained (92%) as a solid: mp 112–122° C.

Analysis for $C_{33}H_{37}N_3O_5S$:
Calculated: C, 67.44; H, 6.35; N, 7.15.
Found: C, 67.24: H, 6.36; N, 7.05.

EXAMPLE 12

3-Methoxy-N-(2-methylphenylsulfonyl)-4-[1-propyl-5-(1-propyl-2-thiopyrrolidin-3-ylmethyl)indol-3-ylmethyl]benzamide a. Methyl 3-methoxy-4-[1-propyl-5-(1-propyl-2-thiopyrrolidin-3-ylmethyl)indol-3-ylmethyl]benzoate 2,4-Bis-(4-methoxyphenyl)-1,3-dithia-2,4-diphosphetane -2,4-disulfide (Lawesson's Reagent, 0.085 g) suspended in dry tetrahydrofuran (2 ml) was added to a stirred solution of methyl 3-methoxy-4-[1-propylyl -5-(1-propyl-2-oxopyrrolidin-3-ylmethyl)indol-3-ylmethyl]benzoate (0.2 g) in tetrahydrofuran (5 ml), under a nitrogen atmosphere. After 3 hours, the solvent was evaporated and the product purified by flash chromatography, eluting with 1:1 ethyl acetate:hexanes, to give methyl 3-methoxy-4-[1-propyl-5-(1 -propyl-2-thiopyrrolidin-3-ylmethyl)indol-3-ylmethyl]benzoate (97%) as an oil: partial NMR (300 MHz, DMSO-$d_6$): 0.81 (m, 6H, 2xCH ), 3.83 (s, 3H, $OCH_3$), 3.91 (s, 3H, $OCH_3$), 3.99–4.06 (m, 4H).

b. 3-Methoxy-4-[1-propyl-5-(1-propyl-2-thiopyrrolidin-3-ylmethyl)indol-3-ylmethyl]benzoic acid Using a similar procedure to that described in Example 1, part g, except starting from methyl 3-methoxy-4-[1-propyl-5-(1-propyl-2-thiopyrrolidin -3-yl-methyl)indol-3-ylmethyl]benzoate, 3-methoxy-4-[1-propyl-5-(1-propyl-2-thiopyrrolidin-3-ylmethyl)indol -3-ylmethyl]benzoic acid was obtained (92%) as a foam; partial NMR (300 MHz, DMSO-$d_6$): 0.82 (m, 6H, $CH_3$), 3.90 (s, 3H, $OCH_3$), 3.99–4.06 (m, 4H).

c. 3-Methoxy-N-(2-methylphenylsulfonyl)-4-[1-propyl-5-(1-propyl-2-thiopyrrolidin-3-ylmethyl)indol-3-ylmethyl]benzamide Using a similar procedure to that described in Example 1, part h, except starting from 3-methoxy-4-[1-propyl-5-(1-propyl-2-thiopyrrolidin-3-ylmethyl)indol -3-ylmethyl]benzoic acid, the title compound was obtained (98%) as a solid; mp 95–105° C.

Analysis for $C_{35}H_{41}N_3O_5S_2$:
Calculated: C, 66.53; H, 6.54; N, 6.65.
Found: C, 66.31; H, 6.58: N, 6.46.

EXAMPLE 13

The following illustrates represenative pharmaceutical dosages forms which may be used for the therapeutic or prophylactic administration of a compound of formula I or of a pharmaceutically acceptable salt thereof (hereinafter referred to as 'Compound X'):

| | | |
|---|---|---|
| (i) | Title | mg/tablet |
| | 'Compound X' | 100.0 |
| | Lactose | 182.75 |
| | Croscarmellose Sodium | 12.0 |
| | Starch | 2.25 |
| | Magnesium stearate | 3.0 |
| (ii) | Table 2 | mg/tablet |
| | 'Compound X" | 20.0 |
| | Microcrystalline Cellulose | 420.0 |
| | Polyvinylpyrrolidone | 14.0 |
| | Starch | 43.0 |
| | Magnesium stearate | 3.0 |
| (iii) | Capsule | mg/capsule |
| | 'Compound X' | 10.0 |
| | Lactose | 488.5 |
| | Magnesium stearate | 1.5 |
| (iv) | Injection 1 | (10 mg/ml) |
| | 'Compound X" (free acid form) | 1.0% w/v |
| | Sodium phosphate | 3.6% w/v |
| | 0.1M Sodium hydroxide solution | 15.0% w/v |
| | Water for injection . . . to 100% | |
| (v) | Injection 2 (Buffered to pH 6) | (1 mg/ml) |
| | 'Compound X' (free acid form) | 0.1% w/v |
| | Sodium phosphate | 2.26% w/v |
| | Citric acid | 0.38% w/v |
| | Polyethylene glycol 400 | 0.38% w/v |
| | Water for injection . . . to 100% | |
| (vi) | Aerosol | mg/ml |
| | 'Compound X' | 0.2 |
| | Sorbitan trioleate | 0.27 |
| | Trichlorofluoromethane | 70.0 |
| | Dichlordifluoromethane | 280.0 |
| | Dichlorodifluoroethane | 1094.0 |

It will be appreciated that the above pharmaceutical compositions may be varied according to well-known pharmaceutical techniques to accomodate differing amounts and types of active ingredient 'Compound X'. The aerosol (vi) may be used in conjunction with a standard, metered dose aerosol dispenser.

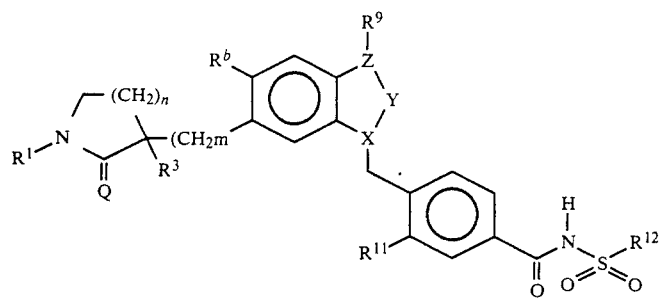
I
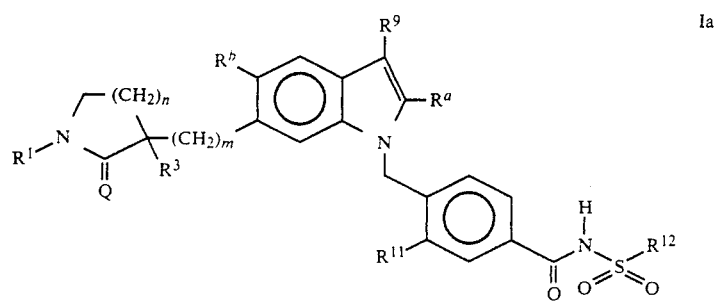
Ia
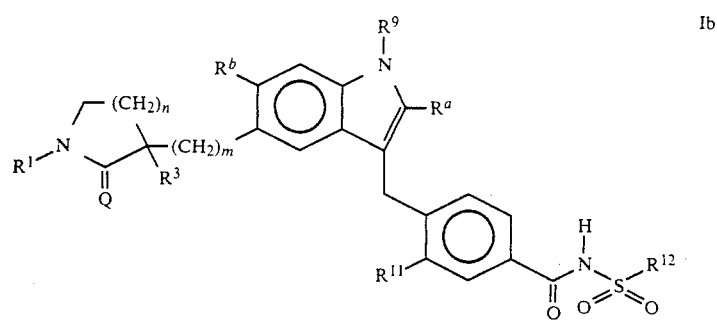
Ib
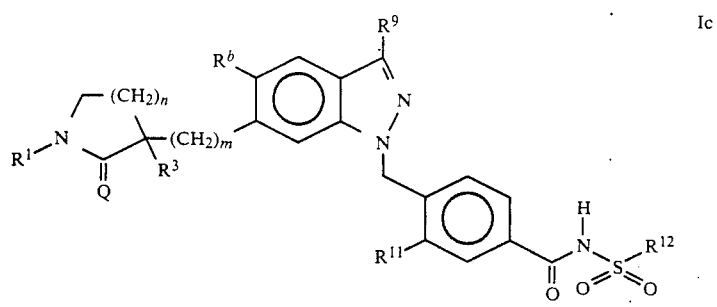
Ic
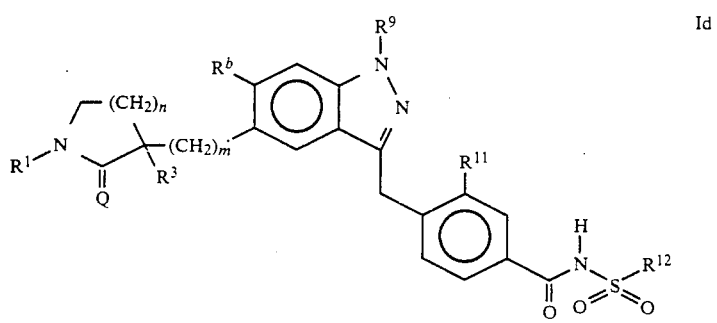
Id

-continued
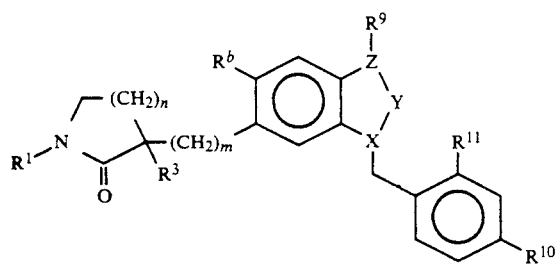
III
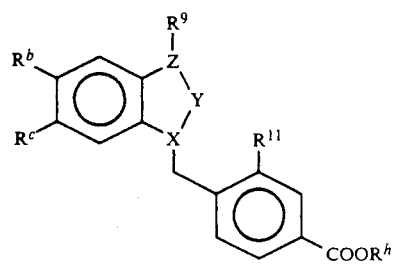
V
SCHEME Ia
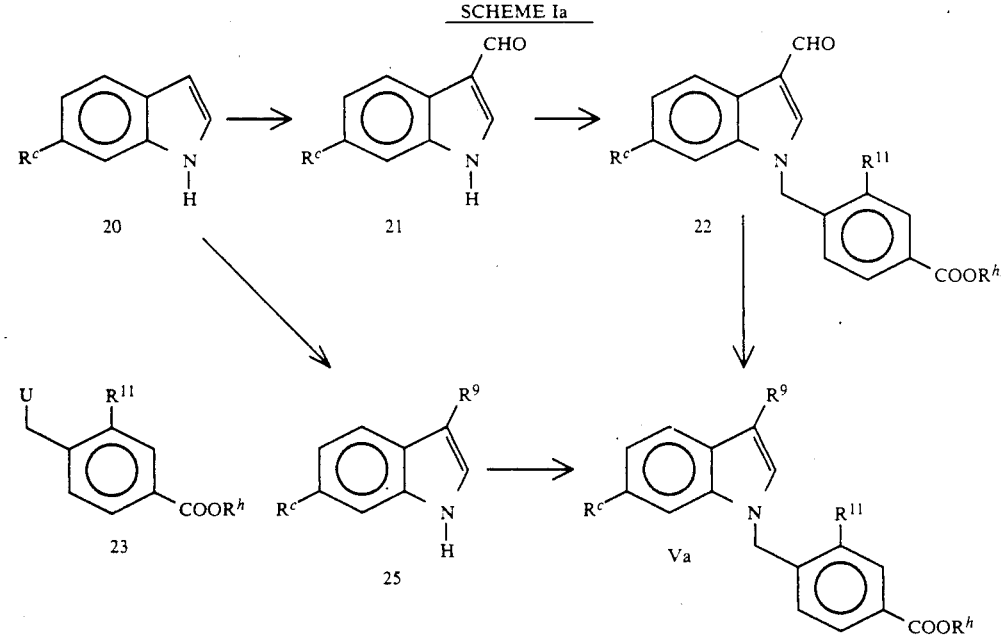
SCHEME Ib
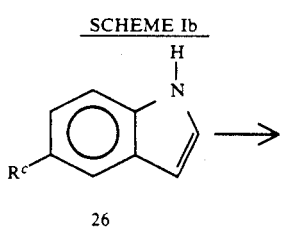
-continued
SCHEME Ib
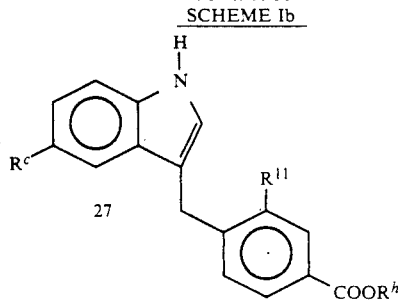

SCHEME Ic
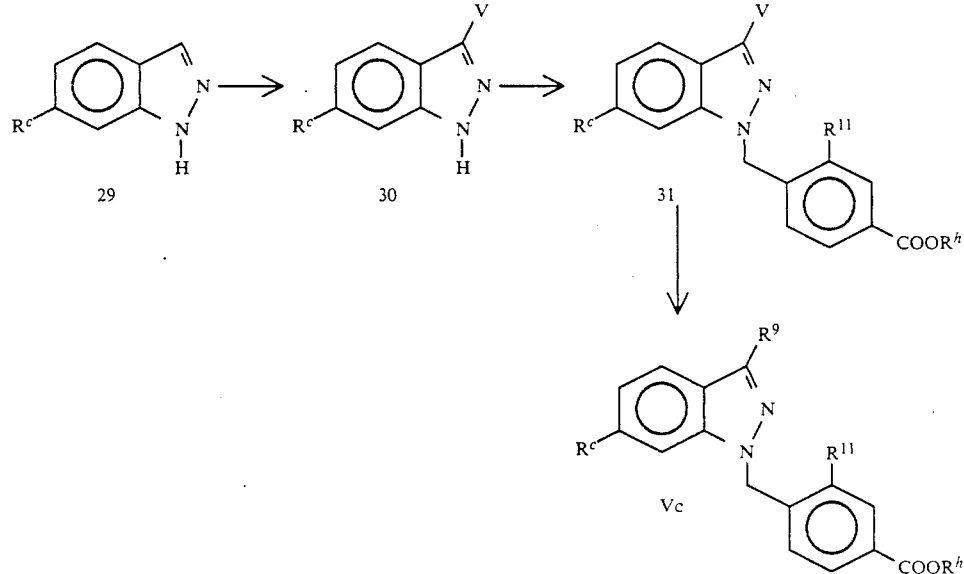
SCHEME Id
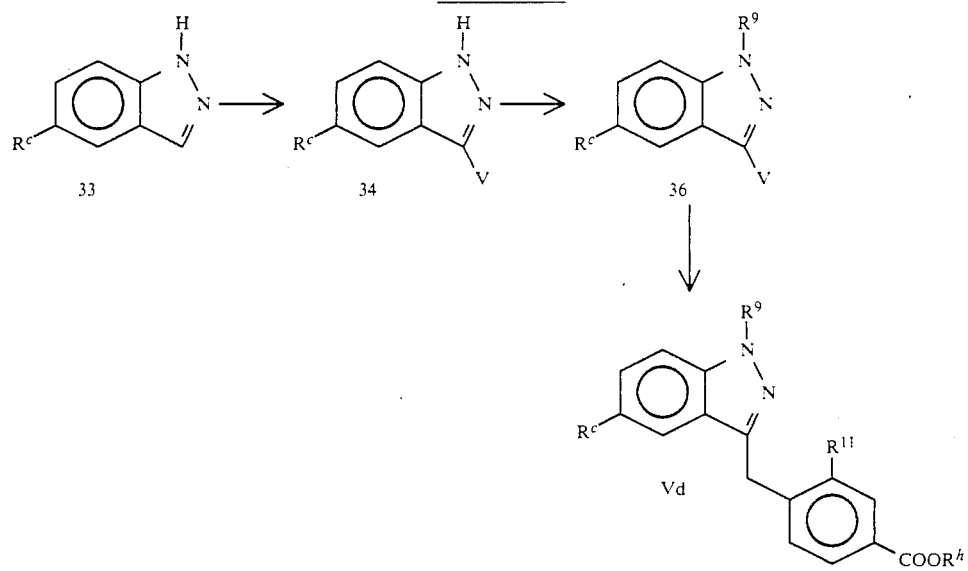
-continued
SCHEME Ib
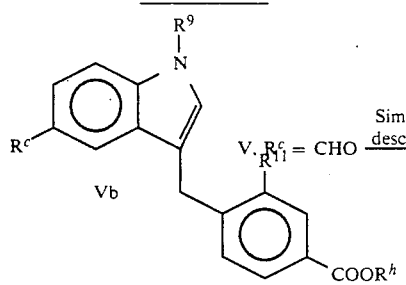
Scheme II
Examples of Routes from a Compound of
Formula V, wherein $R^c$ is formyl (V, $R^c$ = CHO), to a
Compound of Formula III, wherein Q is oxygen and $R^{10}$
is $COOR^h$ (III, Q = O, $R^{10}$ = $COOR^h$):
V, $R^c$ = CHO $\xrightarrow{\text{Similar method to that described in Example 1}}$ III, m = 1, Q = O
$R^{10}$ = $COOR^h$ -continued Scheme II Examples of Routes from a Compound of
Formula V, wherein $R^c$ is formyl (V, $R^c$ = CHO), to a
Compound of Formula III, wherein Q is oxygen and $R^{10}$
is $COOR^h$ (III, Q = O, $R^{10}$ = $COOR^h$):

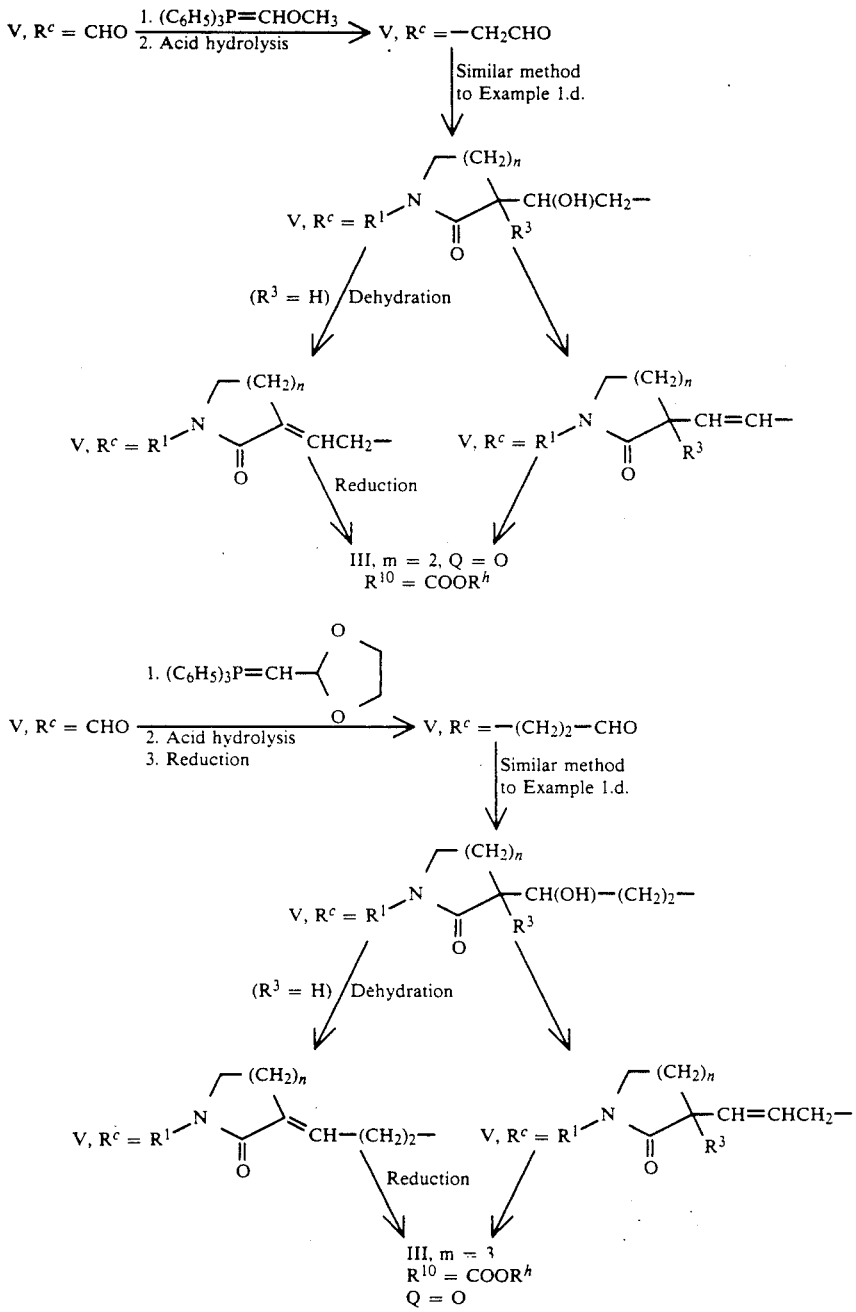

What is claimed is:

1. A compound of formula I, formula set out hereinabove, wherein:
   the group >Z—Y—X< is selected from a group consisting of:
   (a) >C=CR$^a$—N< and
   (b) >N—CR$^a$=C,
   in which ">" indicates two separate bonds;
   the radicals $R^a$ and $R^b$ are together selected from a group consisting of
   (i) $R^a$ and $R^b$ are each hydrogen,
   (ii) $R^a$ is chloro and $R^b$ is hydrogen,
   (iii) $R^a$ is bromo and $R^b$ is hydrogen and
   (iv) $R^a$ and $R^b$ are each chloro;
   Q is oxygen or sulfur;
   the groups $R^1$ and $R^9$ are each independently selected from a group consisting of hydrogen, (1-6C)-alkyl which may contain a double or triple bond,(3-6C-)cycloalkyl and (3-6C)cycloalkyl(1-4C)alkyl wherein a cycloalkyl group or the cycloalkyl portion of a cycloalkylalkyl group may contain a double bond and may bear 1 or 2 (1-3C)alkyl groups;
   $R^3$ is hydrogen or (1-3C)alkyl;

the values of m and n are independently selected from a group of integers consisting of 1, 2 and 3;

$R^{11}$ is selected from a group consisting of hydrogen, (1-4C)alkoxy, (1-2C)alkyl and hydroxy;

$R^{12}$ is selected from a group consisting of (6-12C)aryl, heteroaryl, and (6-12C)aryl(1-4C)alkyl, in any of which the aromatic or heteroaromatic moiety may bear 1 or 2 substituents selected from a group consisting of halogeno, (1-4C)alkyl, (1-4C)alkoxy, trifluoromethyl and amino;

or a salt thereof.

2. A compound as claimed in claim 1 wherein $R^1$ or $R^9$ is, independently, hydrogen, methyl, ethyl, propyl, isopropyl, butyl, 1-methylpropyl, 2-methylpropyl, pentyl, 1-ethylpropyl, 3-methylbutyl, hexyl, 4-methylpentyl, allyl, 2-methylprop-2-enyl, 3-methylbut-3-enyl, 2-propynyl, cyclopropyl, cyclobutyl, cyclopentyl, cyclohexyl, cyclopentenyl, cyclohexenyl, methylcyclobutyl, cyclopropylmethyl, cyclobutylmethyl, cyclopentylmethyl, cyclohexylmethyl, 1-cyclopentylethyl, 2-cyclopentylethyl, or methylcyclopentylethyl;

$R^3$ is hydrogen, methyl, ethyl or propyl;

$R^{11}$ is hydrogen, methoxy, ethoxy propoxy, methyl or ethyl; and $R^{12}$ is phenyl, naphthyl, thienyl, furyl, pyridyl, phenylmethyl, 2-phenylethyl, or 3-phenylpropyl, wherein the aromatic or heteroaromatic portion may bear a fluoro, chloro, bromo, methyl, ethyl, methoxy, ethoxy, trifluoromethyl or amino substituent.

3. A compound as claimed in claim 1 wherein $R^1$ and $R^9$ are each independently selected from a group consisting of hydrogen, (1-4C)alkyl optionally containing a double bond, (3-5C)cycloalkyl and (3-5C)cycloalkyl(1-2C)alkyl;

$R^3$ is hydrogen or methyl;

$R^{11}$ is hydrogen or (1-2C)alkoxy;

$R^{12}$ is phenyl which may bear a methyl, chloro, bromo, fluoro or methoxy group, pyridyl, or thienyl.

4. A compound as claimed in claim 3 wherein $R^a$ is hydrogen or chloro;

$R^b$ is hydrogen;

$R^1$ is methyl, ethyl or propyl;

$R^3$ is hydrogen;

$R^9$ is methyl or propyl;

m is the integer 1;

n is the integer 1 or 2;

$R^{11}$ is methoxy; and $R^{12}$ is 2-methylphenyl, 2-chlorophenyl or 2-bromophenyl.

5. A compound as claimed in claim 1 selected from a group consisting of
 (a) indoles of formula Ia,
 (b) inverted indoles of formula Ib
 (c) indazoles of formula Ic, and
 (d) inverted indazoles of formula Id; and the pharmaceutically acceptable salts thereof, wherein the chemical formulae Ia-Id are set out hereinabove.

6. A compound as claimed in claim 5 which compound is an inverted indole of formula Ib, or a pharmaceutically acceptable salt thereof, wherein the chemical formula Ib is set out hereinabove.

7. A compound as claimed in any of claims 1-6 wherein Q is oxygen, $R^a$ is hydrogen and $R^b$ is hydrogen.

8. A compound as claimed in claim 1 selected from the group consisting of 3-methoxy-N-(2-methylphenylsulfonyl)-4-[1-propyl-5-(1-propyl-2-oxopyrrolidin-3-ylmethyl)indol-3-yl-methyl]benzamide; 3-methoxy-4-[5-(1-methyl-2-oxopiperidin-3-ylmethyl)-1-propylindol-3-ylmethyl]-N-(2-methylphenylsulfonyl)benzamide; and 4-[5-(1-ethyl-2-oxopyrrolidin-3-ylmethyl)-1-propylindol-3-ylmethyl]-3-methoxy-N-(2-methylphenylsulfonyl)benzamide; and the pharmaceutically acceptable salts thereof.

9. A salt as claimed in claim 1 wherein said salt is made with a base forming a physiologically acceptable cation.

10. A pharmaceutical composition comprising a leukotriene antagonizing amount of a compound of claim 1 or a pharmaceutically acceptable salt thereof and a pharmaceutically acceptable diluent or carrier.

11. A composition as claimed in claim 10 wherein said composition is in the form of a liquid or powdered aerosol.

12. A method of antagonizing the action of at least one type of leukotriene in a mammal requiring such treatment comprising administering to said mammal an effective amount of a compound of claim 1.

13. A method for the treatment of a selected allergic or inflammatory disorder in a mammal in need of such treatment comprising administering an effective amount of a compound of claim 1 to such mammal.

14. A compound of formula III, set out hereinabove, wherein $R^{10}$ is carboxy or a group of the formula $COOR^h$ wherein Rh is selected from a group consisting of phenyl, benzyl, and (1-6C)alkyl optionally bearing an acetoxy, (1-4C)alkoxy or (1-4C)alkylthio substituent, and >Z—Y—X<, n, m, Q, M, $R^a$, $R^b$, $R^1$, $R^3$, $R^9$ and $R^{11}$ are defined as in claim 1, or a salt thereof.

* * * * *